US007456264B2

(12) United States Patent
Keler et al.

(10) Patent No.: US 7,456,264 B2
(45) Date of Patent: Nov. 25, 2008

(54) **HUMAN MONOCLONAL ANTIBODIES AGAINST *BACILLUS ANTHRACIS* PROTECTIVE ANTIGEN**

(75) Inventors: Tibor Keler, Ottsville, PA (US); Israel Lowy, Dobbs Ferry, NY (US); Laura A. Vitale, Doylestown, PA (US); Diann Blanset, Hillsborough, NJ (US); Mohan Srinivasan, Cupertino, CA (US)

(73) Assignee: Medarex, Inc., Princeton, NJ (US)

( * ) Notice: Subject to any disclaimer, the term of this patent is extended or adjusted under 35 U.S.C. 154(b) by 659 days.

(21) Appl. No.: 10/850,635

(22) Filed: May 21, 2004

(65) Prior Publication Data

US 2005/0287149 A1    Dec. 29, 2005

Related U.S. Application Data

(60) Provisional application No. 60/512,336, filed on Oct. 16, 2003, provisional application No. 60/472,636, filed on May 21, 2003.

(51) Int. Cl.
*C07K 16/12* (2006.01)
*A61K 39/40* (2006.01)
*G01N 33/569* (2006.01)

(52) U.S. Cl. ............... 530/388.4; 424/142.1; 424/150.1; 436/512; 436/513

(58) Field of Classification Search ........................ None
See application file for complete search history.

(56) References Cited

U.S. PATENT DOCUMENTS

| 4,689,299 A | 8/1987 | Insel et al. | |
|---|---|---|---|
| 2002/0082386 A1 | 6/2002 | Mangold et al. | |
| 2004/0076638 A1* | 4/2004 | Shiloach et al. | 424/190.1 |

FOREIGN PATENT DOCUMENTS

| WO | WO 99/47929 A1 | 9/1999 |
|---|---|---|
| WO | WO 02/46208 A2 | 6/2002 |
| WO | WO-03/040384 A1 | 5/2003 |

OTHER PUBLICATIONS

Greenspan et al. (Nature Biotechnology 17: 936-937, 1999).*
Abbas et al. (Cell. Mol. Immunol. 3rd ed., 1997, p. 45).*
Roitt et al. (Immunol. 3rd ed., 1993, p. 4.8).*
Little, Stephen F. et al., "Characterization of lethal factor binding and cell receptor binding domains of protective antigen of *Bacillus anthracis* using monoclonal antibodies," *Microbiology*, vol. 142:707-715 (1996).
Little, S.F. et al., "Passive Protection by Polyclonal Antibodies against *Bacillus anthracis* Infection in Guinea Pigs," *Infection and Immunity*, vol. 65(12):5171-5175 (1997).
Morrow, Phillip R. et al., "Anthrax Vaccination: A Source for a Panel of Potent Fully Human Monoclonal Antibodies using Xenerex Technology," *National Symposium on Basic Aspects of Vaccines*, May 14-15, 2003.
Rudikoff, Stuart et al., "Single Amino acid substitution altering antigen-binding specificity," *Proc. Natl. Acad. Sci. USA*, vol. 79:1979-1983 (1982).
European Search Report for Application No. 04809410.6-2406, dated Jan. 16, 2007.
Little, S.F. et al., "Production and Characterization of Monoclonal Antibodies Against the Lethal Factor Component of *Bacillus anthracis* Lethal Toxin." *Infection and Immunity*, Jun. 1990, vol. 58, No. 6, pp. 1606-1613.
Cirino, N.M. et al., "Disruption of Anthrax Toxin Binding with the Use of Human Antibodies and Competitive Inhibitors." *Infection and Immunity*, Jun. 1999, vol. 67, No. 6, pp 2957-2963.
Maynard, J.A. et al., "Protection Against Anthrax Toxin by Recombinant Antibody Fragments Correlates with Antigen Affinity." *Nature Biotechnology*, Jun. 2002, vol. 20, pp. 597-601.
Mourez, M. et al., "Designing a Polyvalent Inhibitor of Anthrax Toxin." *Nature Biotechnology*, Oct. 2001, vol. 19, pp. 958-961.
International Search Report to PCT/US04/16213, dated Mar. 24, 2005.
Written Opinion of the International Searching Authority to PCT/US04/16213, dated Mar. 24, 2005.
International Preliminary Examination Report to PCT/US04/16213, dated Dec. 16, 2005.

* cited by examiner

*Primary Examiner*—Shanon A. Foley
*Assistant Examiner*—Brian J Gangle
(74) *Attorney, Agent, or Firm*—Lahive & Cockfield, LLP; Jane E. Remillard, Esq.

(57) ABSTRACT

Isolated human monoclonal antibodies which bind to Anthrax protective antigen are disclosed. The human antibodies can be produced in a non-human transgenic animal, e.g., a transgenic mouse, capable of producing multiple isotypes of human monoclonal antibodies by undergoing V-D-J recombination and isotype switching. Also disclosed are derivatives of the human antibodies (e.g., bispecific antibodies and immunoconjugates), pharmaceutical compositions comprising the human antibodies, non-human transgenic animals and hybridomas which produce the human antibodies, and therapeutic and diagnostic methods for using the human antibodies.

32 Claims, 18 Drawing Sheets

Anti-rPA 5E8VH

V-segment:  VH3-33
    D-segment:  unknown
    J-segment:  JH6b

```
            Q   V   Q   L   V   E   S   G   G   G   V   V   Q   P   G   R   S   L
  1         CAG GTG CAG CTG GTG GAG TCT GGG GGA GGC GTG GTC CAG CCT GGG AGG TCC CTG

CDR 1
                                                                    ---------------------
            R   L   S   C   A   A   S   G   F   T   F   S   Y   Y   G   M   H   W
 55         AGA CTC TCC TGT GCA GCG TCT GGA TTC ACC TTC AGT TAC TAT GGC ATG CAC TGG

CDR 2
                                                                    ---------------------
            V   R   Q   A   P   G   K   G   L   E   W   V   A   V   I   W   H   D
109         GTC CGC CAG GCT CCA GGC AAG GGG CTG GAG TGG GTG GCA GTT ATA TGG CAT GAT

CDR 2
            ------------------------------------------------------------
            E   S   I   V   Y   Y   A   D   S   V   K   G   R   F   T   I   S   R
163         GAA AGT ATT GTA TAC TAT GCA GAC TCC GTG AAG GGC CGA TTC ACC ATC TCC AGA

D   N   S   K   N   T   L   Y   L   Q   M   N   S   L   R   A   E   D
217         GAC AAT TCC AAG AAC ACG CTG TAT CTG CAA ATG AAC AGT CTG AGA GCC GAG GAC

CDR 3
                                                                ------------------------------------------
            T   A   V   Y   Y   C   T   R   D   P   G   D   P   Y   Y   Y   Y   Y
271         ACG GCT GTG TAT TAC TGT ACG AGA GAC CCT GGG GAT CCC TAT TAC TAC TAC TAC

CDR 3
                ------------------
            G   L   D   V   W   G   Q   G   T   T   V   T   V   S   S
325         GGT TTG GAC GTC TGG GGC CAA GGG ACC ACG GTC ACC GTC TCC TCA
```

Figure 1

Anti-rPA 5E8VK (minor)

V-segment:   A27
J-segment:   JK4

```
        E   I   V   L   T   Q   S   P   G   T   L   S   L   S   P   G   E   R
  1     GAA ATT GTG TTG ACG CAG TCT CCA GGC ACC CTG TCT TTG TCT CCA GGG GAA AGA
                                          CDR 1
                               ---------------------------------------------------
        A   T   L   S   C   R   A   S   Q   S   V   S   S   S   Y   L   A   W
 55     GCC ACC CTC TCC TGC AGG GCC AGT CAG AGT GTT AGC AGC AGC TAC TTA GCC TGG
                                                                  CDR 2
                                                              -----------------
        Y   Q   Q   K   P   G   Q   A   P   R   L   L   I   Y   G   A   S   S
109     TAC CAG CAG AAA CCT GGC CAG GCT CCC AGG CTC CTC ATC TAT GGT GCA TCC AGC

CDR 2
        -------------
        R   A   T   G   I   P   D   R   F   S   G   S   G   S   G   T   D   F
163     AGG GCC ACT GGC ATC CCA GAC AGG TTC AGT GGC AGT GGG TCT GGG ACA GAC TTC
                                                                          CDR 3
                                                                          ---
        T   L   T   I   S   R   L   E   P   E   D   F   A   V   Y   Y   C   Q
217     ACT CTC ACC ATC AGC AGA CTG GAG CCT GAA GAT TTT GCA GTG TAT TAC TGT CAG

CDR 3
        ---------------------------------
        Q   Y   G   S   S   P   P   T   F   G   G   G   T   K   V   E   I   K
271     CAG TAT GGT AGC TCA CCT CCC ACT TTC GGC GGA GGG ACC AAG GTG GAG ATC AAA
```

Figure 2

Anti-rPA 5E8VK (major)

V-segment: A27
    J-segment: JK2

```
            E   I   V   L   T   Q   S   P   G   T   L   S   L   S   P   G   E   R
  1        GAA ATT GTG TTG ACG CAG TCT CCA GGC ACC CTG TCT TTG TCT CCA GGG GAA AGA
                                                           CDR 1
                                                  -----------------------------------------------------
            A   T   L   S   C   R   A   S   Q   S   V   S   S   S   Y   L   A   W
 55        GCC ACC CTC TCC TGC AGG GCC AGT CAG AGT GTT AGC AGC AGC TAC TTA GCC TGG
                                                                               CDR 2
                                                                           -------------------
            Y   Q   Q   K   P   G   Q   A   P   R   L   L   I   Y   G   A   S   S
109        TAC CAG CAG AAA CCT GGC CAG GCT CCC AGG CTC CTC ATC TAT GGT GCA TCC AGC

CDR 2
            ---------------
            R   A   T   G   I   P   D   R   F   S   G   S   G   S   G   T   D   F
163        AGG GCC ACT GGC ATC CCA GAC AGG TTC AGT GGC AGT GGG TCT GGG ACA GAC TTC
                                                                                CDR 3
                                                                                ---
            T   L   T   I   S   R   L   E   P   E   D   F   A   V   Y   Y   C   Q
217 ACT CTC ACC ATC AGC AGA CTG GAG CCT GAA GAT TTT GCA GTG TAT TAC TGT CAG
                CDR 3
            -----------------------------------------
            Q   Y   G   S   S   M   Y   T   F   G   Q   G   T   K   L   E   I   K
271        CAG TAT GGT AGC TCA ATG TAC ACT TTT GGC CAG GGG ACC AAG CTA GAG ATC AAA
```

Figure 3

Anti-rPA 2D5VH

V-segment: VH3-33
    D-segment: D7-27
    J-segment: JH4b

```
         Q   V   Q   L   V   E   S   G   G   G   V   V   Q   P   G   R   S   L
   1     CAG GTG CAG CTG GTG GAG TCT GGG GGA GGC GTG GTC CAG CCT GGG AGG TCC CTG

CDR 1
                                                                  ---------------
         R   L   S   C   A   A   S   G   F   T   F   S   S   Y   G   M   H   W
  55     AGA CTC TCC TGT GCA GCG TCT GGA TTC ACC TTC AGT AGC TAT GGC ATG CAC TGG

CDR 2
                                                                  ---------------
         V   R   Q   A   P   G   K   G   L   E   W   V   A   V   I   W   N   D
 109     GTC CGC CAG GCT CCA GGC AAG GGG CTG GAG TGG GTG GCA GTT ATA TGG AAT GAT

CDR 2
         ----------------------------------------
         G   S   N   K   Y   Y   A   D   S   V   K   G   R   F   T   I   S   R
 163     GGA AGT AAT AAA TAC TAT GCA GAC TCC GTG AAG GGC CGA TTC ACC ATC TCC AGA

D   N   S   K   N   T   L   Y   L   Q   M   N   S   L   R   A   E   D
 217     GAC AAT TCC AAG AAC ACG CTG TAT CTG CAA ATG AAC AGC CTG AGA GCC GAG GAC

CDR 3
                                           ----------------------------------------
         T   A   V   Y   Y   C   A   R   E   N   W   G   E   Y   F   D   Y   W
 271     ACG GCT GTG TAT TAC TGT GCG AGA GAA AAC TGG GGA GAG TAC TTT GAC TAC TGG

G   Q   G   T   L   V   T   V   S   S
 325     GGC CAG GGA ACC CTG GTC ACC GTC TCC TCA
```

Figure 4

Anti-rPA 2D5VK

V-segment: L18
    J-segment: JK1

```
      A   I   Q   L   T   Q   S   P   S   S   L   S   A   S   V   G   D   R
  1   GCC ATC CAG TTG ACC CAG TCT CCA TCC TCC CTG TCT GCA TCT GTA GGA GAC AGA

CDR 1
                              ----------------------------------------------
      V   T   I   T   C   R   A   S   Q   G   I   S   S   A   L   A   W   Y
 55   GTC ACC ATC ACT TGC CGG GCA AGT CAG GGC ATT AGC AGT GCT TTA GCC TGG TAT

CDR 2
                                                  ------------------------
      Q   Q   K   P   G   K   A   P   K   L   L   I   Y   D   A   S   S   L
109   CAG CAG AAA CCA GGG AAA GCT CCT AAG CTC CTG ATC TAT GAT GCC TCC AGT TTG

CDR 2
      --------
      K   S   G   V   P   S   R   F   S   G   S   G   S   G   T   D   F   T
163   AAA AGT GGG GTC CCA TCA AGG TTC AGC GGC AGT GGA TCT GGG ACA GAT TTC ACT

CDR 3
                                                                      -------
      L   T   I   S   S   L   Q   P   E   D   F   A   T   Y   Y   C   Q   Q
217   CTC ACC ATC AGC AGC CTG CAG CCT GAA GAT TTT GCA ACT TAT TAC TGT CAA CAG

CDR 3
      -------------------------
      F   N   S   Y   W   T   F   G   Q   G   T   K   V   E   I   K
271   TTT AAT AGT TAC TGG ACG TTC GGC CAA GGG ACC AAG GTG GAA ATC AAA
```

Figure 5

Anti-rPA 2H4VH

V-segment:   VH3-7
    D-segment:   D3-10
    J-segment:   JH2

```
                E   V   H   L   V   E   S   G   G   G   L   V   Q   P   G   G   S   L
    1          GAG GTG CAC CTG GTG GAG TCT GGG GGA GGC TTG GTC CAG CCT GGG GGG TCC CTG
                                                                        CDR 1
                                                                        ---------------------
                R   L   S   C   A   A   S   G   F   T   F   S   S   Y   W   M   S   W
    55         AGA CTC TCC TGT GCA GCC TCT GGA TTC ACC TTT AGT AGC TAT TGG ATG AGC TGG
                                                                        CDR 2
                                                                        ---------------------
                V   R   Q   A   P   G   K   G   L   E   W   V   A   N   I   N   Q   Y
    109        GTC CGC CAG GCT CCA GGG AAA GGG CTG GAG TGG GTG GCC AAC ATA AAT CAA TAT
                            CDR 2
                ------------------------------------------------------
                G   S   E   K   Y   Y   V   D   S   V   K   G   R   F   T   I   S   R
    163        GGA AGT GAG AAA TAC TAT GTG GAC TCT GTG AAG GGC CGA TTC ACC ATC TCC AGA

D   N   A   K   N   S   L   Y   L   Q   M   N   S   L   R   A   E   D
    217        GAC AAC GCC AAG AAC TCG CTG TAT CTG CAA ATG AAC AGC CTG AGA GCC GAG GAC
                                                                        CDR 3
                                                                        ---------------------
                T   A   V   Y   Y   C   A   R   D   S   P   Y   Y   Y   G   S   G   S
    271        ACG GCT GTG TAT TAC TGT GCG AGG GAC TCC CCG TAT TAC TAT GGT TCG GGG AGT
                                    CDR3
                ------------------------------------------------------
                Y   Y   R   G   Y   W   Y   F   D   L   W   G   R   G   T   L   V   T
    325        TAT TAT AGA GGA TAC TGG TAC TTC GAT CTC TGG GGC CGT GGC ACC CTG GTC ACT

V   S   S
    379        GTC TCC TCA
```

Figure 6

Anti-rPA 2H4VK

V-segment:   L15
    J-segment:   JK5

```
              D   I   Q   M   T   Q   S   P   S   S   L   S   A   S   V   G   D   R
  1          GAC ATC CAG ATG ACC CAG TCT CCA TCC TCA CTG TCT GCA TCT GTA GGA GAC AGA
                                                    CDR 1
                                              ---------------------------------------
              V   T   I   T   C   R   A   S   Q   G   I   S   S   W   L   A   W   Y
 55          GTC ACC ATC ACT TGT CGG GCG AGT CAG GGT ATT AGC AGC TGG TTA GCC TGG TAT
                                                                            CDR 2
                                                                      -----------------
              Q   Q   K   P   E   K   A   P   K   S   L   I   Y   A   A   S   S   L
109          CAG CAG AAA CCA GAG AAA GCC CCT AAG TCC CTG ATC TAT GCT GCA TCC AGT TTG

CDR 2
             --------
              Q   S   G   V   P   S   R   F   S   G   S   G   S   G   T   D   F   T
163          CAA AGT GGG GTC CCA TCA AGG TTC AGC GGC AGT GGA TCT GGG ACA GAT TTC ACT
                                                                            CDR 3
                                                                            --------
              L   T   I   S   S   L   Q   P   E   D   F   A   T   Y   Y   C   Q   Q
217          CTC ACC ATC AGC AGC CTG CAG CCT GAA GAT TTT GCA ACT TAT TAC TGC CAA CAG

CDR 3
             --------------------------------
              Y   N   S   Y   P   P   T   F   G   Q   G   T   R   L   E   I   K
271          TAT AAT AGT TAC CCT CCC ACC TTC GGC CAA GGG ACA CGA CTG GAG ATT AAA
```

Figure 7

Anti-rPA 5D5-2E10 VH

V-segment:   VH3-33
    D-segment:   not found
    J-segment:   JH4b

```
            Q   V   Q   L   V   E   S   G   G   G   V   V   Q   P   G   R   S   L
  1        CAG GTG CAG CTG GTG GAG TCT GGG GGA GGC GTG GTC CAG CCT GGG AGG TCC CTG

CDR 1
                                                                    --------------------
            R   L   S   C   A   A   S   G   F   T   F   S   S   Y   G   M   H   W
 55        AGA CTC TCC TGT GCA GCG TCT GGA TTC ACC TTC AGT AGC TAT GGC ATG CAC TGG

CDR 2
                                                                    --------------------
            V   R   Q   A   P   G   K   G   L   E   W   V   A   V   I   W   Y   D
109        GTC CGC CAG GCT CCA GGC AAG GGG CTG GAG TGG GTG GCA GTT ATA TGG TAT GAT

CDR 2
           ---------------------------------------------------
            G   S   N   K   Y   Y   A   D   S   V   K   G   R   F   T   I   S   R
163        GGA AGT AAT AAA TAC TAT GCA GAC TCC GTG AAG GGC CGA TTC ACC ATC TCC AGA

D   N   S   K   N   T   L   Y   L   Q   M   N   S   L   R   A   E   D
217        GAC AAT TCC AAG AAC ACG CTG TAT CTG CAA ATG AAC AGC CTG AGA GCC GAG GAC

CDR 3
                                                                ------------------------
            T   A   V   Y   Y   C   A   R   E   G   N   R   S   H   Y   I   P   F
271        ACG GCT GTG TAT TAC TGT GCG AGA GAG GGT AAT CGT AGC CAC TAT ATA CCC TTT

CDR 3
           ---------
            A   Y   W   G   Q   G   T   L   V   T   V   S   S
325        GCC TAC TGG GGC CAG GGA ACC CTG GTC ACC GTC TCC TCA
```

Figure 8

Anti-rPA 5D5-2E10 VK

V-segment: L15
    J-segment: JK4

```
          D   I   Q   M   T   Q   S   P   S   S   L   S   A   S   V   G   D   R
  1      GAC ATC CAG ATG ACC CAG TCT CCA TCC TCA CTG TCT GCA TCT GTA GGA GAC AGA

CDR 1
                             ---------------------------------------------------
          V   T   I   T   C   R   A   S   Q   G   I   S   S   W   L   A   W   Y
 55      GTC ACC ATC ACT TGT CGG GCG AGT CAG GGT ATT AGC AGC TGG TTA GCC TGG TAT

CDR 2
                                                                    -------------------
          Q   Q   K   P   E   K   A   P   K   S   L   I   Y   A   A   S   S   L
109      CAG CAG AAA CCA GAG AAA GCC CCT AAG TCC CTG ATC TAT GCT GCA TCC AGT TTG

CDR 2
         --------
          Q   S   G   V   P   S   R   F   S   G   S   G   S   G   T   D   F   T
163      CAA AGT GGG GTC CCA TCA AGG TTC AGC GGC AGT GGA TCT GGG ACA GAT TTC ACT

CDR 3
                                                                            -------
          L   T   I   S   S   L   Q   P   E   D   F   A   T   Y   Y   C   Q   Q
217      CTC ACC ATC AGC AGC CTG CAG CCT GAA GAT TTT GCA ACT TAT TAC TGC CAA CAG

CDR 3
         -------------------------------
          Y   N   S   Y   P   R   T   F   G   G   G   T   K   V   E   I   K
271      TAT AAT AGT TAC CCG CGC ACT TTC GGC GGA GGG ACC AAG GTG GAG ATC AAA
```

**In vitro toxin neutralization:
HuMab 5E8 protects cells after addition of toxin**

ELISA assay :
HuMAb 5E8 Binds to PA63 at a unique epitope

Legend: Isotype Control | Mu MAb no block | Mu MAb + 5E8 HuMab

| Mu Mab: | 14B7 | 2D5 | 1G3 |
|---|---|---|---|
| binding epitope : | 671-721aa | 581-601aa | 168-314aa |
| | Blocks receptor binding | Block LF binding | |

FIGURE 15

SEQUENCE LISTING

```
<160> NUMBER OF SEQ ID NOS: 72

<210> SEQ ID NO 1
<211> LENGTH: 369
<212> TYPE: DNA
<213> ORGANISM: Homo sapiens

<400> SEQUENCE: 1
caggtgcagc tggtggagtc tgggggaggc gtggtccagc ctggaggtc cctgagactc      60 tcctgtgcag cgtctggatt caccttcagt tactatggca tgcactgggt ccgccaggct    120
ccaggcaagg ggctggagtg ggtggcagtt atatggcatg atgaaagtat tgtatactat    180
gcagactccg tgaagggccg attcaccatc tccagagaca attccaagaa cacgctgtat    240
ctgcaaatga acagtctgag agccgaggac acggctgtgt attactgtac gagagaccct    300
ggggatccct attactacta ctacggtttg gacgtctggg gccaagggac cacggtcacc    360
gtctcctca                                                            369

<210> SEQ ID NO 2
<211> LENGTH: 123
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Tyr Tyr
                 20                  25                  30

Gly Met His Trp Val Arg Gln Ala Pro Gly Lys Gly Leu Glu Trp Val
             35                  40                  45

Ala Val Ile Trp His Asp Glu Ser Ile Val Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Asp Pro Gly Asp Pro Tyr Tyr Tyr Tyr Gly Leu Asp Val
                100                 105                 110

Trp Gly Gln Gly Thr Thr Val Thr Val Ser Ser
            115                 120

<210> SEQ ID NO 3
<211> LENGTH: 324
<212> TYPE: DNA
<213> ORGANISM: Homo sapiens

<400> SEQUENCE: 3
gaaattgtgt tgacgcagtc tccaggcacc ctgtctttgt ctccagggga aagagccacc     60
```

```
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacctcc cactttcggc    300
ggagggacca aggtggagat caaa                                           324
```

<210> SEQ ID NO 4
<211> LENGTH: 108
<212> TYPE: PRT
<213> ORGANISM: Homo sapiens

<400> SEQUENCE: 4

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Thr Phe Gly Gly Gly Thr Lys Val Glu Ile Lys
            100                 105
```

<210> SEQ ID NO 5
<211> LENGTH: 324
<212> TYPE: DNA
<213> ORGANISM: Homo sapiens

<400> SEQUENCE: 5

```
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaatgta cacttttggc    300
cagggaccaa gctagagat caaa                                            324
```

<210> SEQ ID NO 6
<211> LENGTH: 108
<212> TYPE: PRT
<213> ORGANISM: Homo sapiens

<400> SEQUENCE: 6

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60
```

-continued

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Met
                85                  90                  95

Tyr Thr Phe Gly Gln Gly Thr Lys Leu Glu Ile Lys
            100                 105

<210> SEQ ID NO 7
<211> LENGTH: 354
<212> TYPE: DNA
<213> ORGANISM: Homo sapiens

<400> SEQUENCE: 7
caggtgcagc tggtggagtc tgggggaggc gtggtccagc ctggggaggtc cctgagactc      60 tcctgtgcag cgtctggatt caccttcagt agctatggca tgcactgggt ccgccaggct     120
ccaggcaagg ggctggagtg ggtggcagtt atatggaatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagaaaac     300
tggggagagt actttgacta ctggggccag ggaaccctgg tcaccgtctc ctca           354

<210> SEQ ID NO 8
<211> LENGTH: 118
<212> TYPE: PRT
<213> ORGANISM: Homo sapiens

<400> SEQUENCE: 8

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Trp Gly Glu Tyr Phe Asp Tyr Trp Gly Gln Gly Thr
            100                 105                 110

Leu Val Thr Val Ser Ser
        115

<210> SEQ ID NO 9
<211> LENGTH: 318
<212> TYPE: DNA
<213> ORGANISM: Homo sapiens

<400> SEQUENCE: 9
gccatccagt tgacccagtc tccatcctcc ctgtctgcat ctgtaggaga cagagtcacc      60
atcacttgcc gggcaagtca gggcattagc agtgctttag cctggtatca gcagaaacca     120
gggaaagctc ctaagctcct gatctatgat gcctccagtt tgaaaagtgg ggtcccatca     180
aggttcagcg gcagtggatc tgggacagat ttcactctca ccatcagcag cctgcagcct     240
gaagattttg caacttatta ctgtcaacag tttaatagtt actggacgtt cggccaaggg     300
accaaggtgg aaatcaaa 318

<210> SEQ ID NO 10
<211> LENGTH: 106
<212> TYPE: PRT
<213> ORGANISM: Homo sapiens

<400> SEQUENCE: 10

```
Ala Ile Gln Leu Thr Gln Ser Pro Ser Ser Leu Ser Ala Ser Val Gly
 1               5                  10                  15
Asp Arg Val Thr Ile Thr Cys Arg Ala Ser Gln Gly Ile Ser Ser Ala
            20                  25                  30
Leu Ala Trp Tyr Gln Gln Lys Pro Gly Lys Ala Pro Lys Leu Leu Ile
        35                  40                  45
Tyr Asp Ala Ser Ser Leu Lys Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Asn Ser Tyr Trp Thr
                85                  90                  95
Phe Gly Gln Gly Thr Lys Val Glu Ile Lys
            100                 105
```

<210> SEQ ID NO 11
<211> LENGTH: 387
<212> TYPE: DNA
<213> ORGANISM: Homo sapiens

<400> SEQUENCE: 11
gaggtgcacc tggtggagtc tgggggaggc ttggtccagc ctggggggtc cctgagactc 60
tcctgtgcag cctctggatt cacctttagt agctattgga tgagctgggt ccgccaggct 120
ccagggaaag ggctggagtg ggtggccaac ataaatcaat atggaagtga aaatactat 180 gtggactctg tgaagggccg attcaccatc tccagagaca acgccaagaa ctcgctgtat 240
ctgcaaatga acagcctgag agccgaggac acggctgtgt attactgtgc gagggactcc 300
ccgtattact atggttcggg gagttattat agaggatact ggtacttcga tctctggggc 360
cgtggcaccc tggtcactgt ctcctca 387

<210> SEQ ID NO 12
<211> LENGTH: 129
<212> TYPE: PRT
<213> ORGANISM: Homo sapiens

<400> SEQUENCE: 12

```
Glu Val His Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Trp Met Ser Trp Val Arg Gln Ala Pro Gly Lys Gly Leu Glu Trp Val
        35                  40                  45
Ala Asn Ile Asn Gln Tyr Gly Ser Glu Lys Tyr Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
```

Ala Arg Asp Ser Pro Tyr Tyr Tyr Gly Ser Gly Ser Tyr Tyr Arg Gly
            100                 105                 110

Tyr Trp Tyr Phe Asp Leu Trp Gly Arg Gly Thr Leu Val Thr Val Ser
        115                 120                 125

Ser

<210> SEQ ID NO 13
<211> LENGTH: 321
<212> TYPE: DNA
<213> ORGANISM: Homo sapiens

<400> SEQUENCE: 13

```
gacatccaga tgacccagtc tccatcctca ctgtctgcat ctgtaggaga cagagtcacc      60
atcacttgtc gggcgagtca gggtattagc agctggttag cctggtatca gcagaaacca    120
gagaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacag tataatagtt accctcccac cttcggccaa    300
gggacacgac tggagattaa a                                              321
```

<210> SEQ ID NO 14
<211> LENGTH: 107
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Arg Leu Glu Ile Lys
            100                 105

<210> SEQ ID NO 15
<211> LENGTH: 363
<212> TYPE: DNA
<213> ORGANISM: Homo sapiens

<400> SEQUENCE: 15

```
caggtgcagc tggtggagtc tgggggaggc gtggtccagc ctgggaggtc cctgagactc      60
tcctgtgcag cgtctggatt caccttcagt agctatggca tgcactgggt ccgccaggct    120
ccaggcaagg ggctggagtg ggtggcagtt atatggtatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagagggt    300
aatcgtagcc actatatacc ctttgcctac tggggccagg gaaccctggt caccgtctcc    360
tca                                                                  363
```

<210> SEQ ID NO 16
<211> LENGTH: 121
<212> TYPE: PRT
<213> ORGANISM: Homo sapiens

<400> SEQUENCE: 16

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asn Arg Ser His Tyr Ile Pro Phe Ala Tyr Trp Gly
            100                 105                 110

Gln Gly Thr Leu Val Thr Val Ser Ser
        115                 120

<210> SEQ ID NO 17
<211> LENGTH: 321
<212> TYPE: DNA
<213> ORGANISM: Homo sapiens

<400> SEQUENCE: 17
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgccaacag tataatagtt acccgcgcac tttcggcgga     300
gggaccaagg tggagatcaa a                                               321

<210> SEQ ID NO 18
<211> LENGTH: 107
<212> TYPE: PRT
<213> ORGANISM: Homo sapiens

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gly Gly Thr Lys Val Glu Ile Lys
            100                 105

<210> SEQ ID NO 19
<211> LENGTH: 42
<212> TYPE: DNA
<213> ORGANISM: Homo sapiens

<400> SEQUENCE: 19
gaccctgggg atccctatta ctactactac ggtttggacg tc            42

<210> SEQ ID NO 20
<211> LENGTH: 14
<212> TYPE: PRT
<213> ORGANISM: Homo sapiens

<400> SEQUENCE: 20

Asp Pro Gly Asp Pro Tyr Tyr Tyr Tyr Gly Leu Asp Val
 1               5                   10

<210> SEQ ID NO 21
<211> LENGTH: 51
<212> TYPE: DNA
<213> ORGANISM: Homo sapiens

<400> SEQUENCE: 21
gttatatggc atgatgaaag tattgtatac tatgcagact ccgtgaaggg c        51

<210> SEQ ID NO 22
<211> LENGTH: 17
<212> TYPE: PRT
<213> ORGANISM: Homo sapiens

<400> SEQUENCE: 22

Val Ile Trp His Asp Glu Ser Ile Val Tyr Tyr Ala Asp Ser Val Lys
 1               5                   10                  15
Gly

<210> SEQ ID NO 23
<211> LENGTH: 15
<212> TYPE: DNA
<213> ORGANISM: Homo sapiens

<400> SEQUENCE: 23
tactatggca tgcac                    15

<210> SEQ ID NO 24
<211> LENGTH: 5
<212> TYPE: PRT
<213> ORGANISM: Homo sapiens

<400> SEQUENCE: 24

Tyr Tyr Gly Met His
 1               5

<210> SEQ ID NO 25
<211> LENGTH: 27
<212> TYPE: DNA
<213> ORGANISM: Homo sapiens

<400> SEQUENCE: 25
cagcagtatg gtagctcacc tcccact                    27

```
<210> SEQ ID NO 26
<211> LENGTH: 9
<212> TYPE: PRT
<213> ORGANISM: Homo sapiens

<400> SEQUENCE: 26

Gln Gln Tyr Gly Ser Ser Pro Pro Thr
 1               5

<210> SEQ ID NO 27
<211> LENGTH: 21
<212> TYPE: DNA
<213> ORGANISM: Homo sapiens

<400> SEQUENCE: 27
ggtgcatcca gcagggccac t                                              21

<210> SEQ ID NO 28
<211> LENGTH: 7
<212> TYPE: PRT
<213> ORGANISM: Homo sapiens

<400> SEQUENCE: 28

Gly Ala Ser Ser Arg Ala Thr
 1               5

<210> SEQ ID NO 29
<211> LENGTH: 36
<212> TYPE: DNA
<213> ORGANISM: Homo sapiens

<400> SEQUENCE: 29
agggccagtc agagtgttag cagcagctac ttagcc                              36

<210> SEQ ID NO 30
<211> LENGTH: 12
<212> TYPE: PRT
<213> ORGANISM: Homo sapiens

<400> SEQUENCE: 30

Arg Ala Ser Gln Ser Val Ser Ser Ser Tyr Leu Ala
 1               5                  10

<210> SEQ ID NO 31
<211> LENGTH: 27
<212> TYPE: DNA
<213> ORGANISM: Homo sapiens

<400> SEQUENCE: 31
cagcagtatg gtagctcaat gtacact                                        27

<210> SEQ ID NO 32
<211> LENGTH: 9
<212> TYPE: PRT
<213> ORGANISM: Homo sapiens

<400> SEQUENCE: 32

Gln Gln Tyr Gly Ser Ser Met Tyr Thr
 1               5

<210> SEQ ID NO 33
<211> LENGTH: 21
<212> TYPE: DNA
<213> ORGANISM: Homo sapiens
```

<400> SEQUENCE: 33
ggtgcatcca gcagggccac t                                             21

<210> SEQ ID NO 34
<211> LENGTH: 7
<212> TYPE: PRT
<213> ORGANISM: Homo sapiens

<400> SEQUENCE: 34

Gly Ala Ser Ser Arg Ala Thr
 1               5

<210> SEQ ID NO 35
<211> LENGTH: 36
<212> TYPE: DNA
<213> ORGANISM: Homo sapiens

<400> SEQUENCE: 35
agggccagtc agagtgttag cagcagctac ttagcc                             36

<210> SEQ ID NO 36
<211> LENGTH: 12
<212> TYPE: PRT
<213> ORGANISM: Homo sapiens

<400> SEQUENCE: 36

Arg Ala Ser Gln Ser Val Ser Ser Ser Tyr Leu Ala
 1               5                  10

<210> SEQ ID NO 37
<211> LENGTH: 27
<212> TYPE: DNA
<213> ORGANISM: Homo sapiens

<400> SEQUENCE: 37
gaaaactggg gagagtactt tgactac                                       27

<210> SEQ ID NO 38
<211> LENGTH: 9
<212> TYPE: PRT
<213> ORGANISM: Homo sapiens

<400> SEQUENCE: 38

Glu Asn Trp Gly Glu Tyr Phe Asp Tyr
 1               5

<210> SEQ ID NO 39
<211> LENGTH: 51
<212> TYPE: DNA
<213> ORGANISM: Homo sapiens

<400> SEQUENCE: 39
gttatatgga atgatggaag taataaatac tatgcagact ccgtgaaggg c             51

<210> SEQ ID NO 40
<211> LENGTH: 12
<212> TYPE: PRT
<213> ORGANISM: Homo sapiens

<400> SEQUENCE: 40

Gly Ser Asn Lys Tyr Tyr Ala Asp Ser Val Lys Gly
 1               5                  10

```
<210> SEQ ID NO 41
<211> LENGTH: 15
<212> TYPE: DNA
<213> ORGANISM: Homo sapiens

<400> SEQUENCE: 41
agctatggca tgcac                                                          15

<210> SEQ ID NO 42
<211> LENGTH: 5
<212> TYPE: PRT
<213> ORGANISM: Homo sapiens

<400> SEQUENCE: 42

Ser Tyr Gly Met His
 1               5

<210> SEQ ID NO 43
<211> LENGTH: 24
<212> TYPE: DNA
<213> ORGANISM: Homo sapiens

<400> SEQUENCE: 43
caacagttta atagttactg gacg                                                24

<210> SEQ ID NO 44
<211> LENGTH: 8
<212> TYPE: PRT
<213> ORGANISM: Homo sapiens

<400> SEQUENCE: 44

Gln Gln Phe Asn Ser Tyr Trp Thr
 1               5

<210> SEQ ID NO 45
<211> LENGTH: 21
<212> TYPE: DNA
<213> ORGANISM: Homo sapiens

<400> SEQUENCE: 45
gatgcctcca gtttgaaaag t                                                   21

<210> SEQ ID NO 46
<211> LENGTH: 7
<212> TYPE: PRT
<213> ORGANISM: Homo sapiens

<400> SEQUENCE: 46

Asp Ala Ser Ser Leu Lys Ser
 1               5

<210> SEQ ID NO 47
<211> LENGTH: 33
<212> TYPE: DNA
<213> ORGANISM: Homo sapiens

<400> SEQUENCE: 47
cgggcaagtc agggcattag cagtgcttta gcc                                      33

<210> SEQ ID NO 48
<211> LENGTH: 11
<212> TYPE: PRT
<213> ORGANISM: Homo sapiens

<400> SEQUENCE: 48
```

```
Arg Ala Ser Gln Gly Ile Ser Ser Ala Leu Ala
 1               5                  10
```

<210> SEQ ID NO 49
<211> LENGTH: 60
<212> TYPE: DNA
<213> ORGANISM: Homo sapiens

<400> SEQUENCE: 49
gactccccgt attactatgg ttcggggagt tattatagag gatactggta cttcgatctc     60

<210> SEQ ID NO 50
<211> LENGTH: 20
<212> TYPE: PRT
<213> ORGANISM: Homo sapiens

<400> SEQUENCE: 50

```
Asp Ser Pro Tyr Tyr Tyr Gly Ser Gly Ser Tyr Tyr Arg Gly Tyr Trp
 1               5                  10                  15

Tyr Phe Asp Leu
            20
```

<210> SEQ ID NO 51
<211> LENGTH: 51
<212> TYPE: DNA
<213> ORGANISM: Homo sapiens

<400> SEQUENCE: 51
aacataaatc aatatggaag tgagaaatac tatgtggact ctgtgaaggg c              51

<210> SEQ ID NO 52
<211> LENGTH: 17
<212> TYPE: PRT
<213> ORGANISM: Homo sapiens

<400> SEQUENCE: 52

```
Asn Ile Asn Gln Tyr Gly Ser Glu Lys Tyr Tyr Val Asp Ser Val Lys
 1               5                  10                  15

Gly
```

<210> SEQ ID NO 53
<211> LENGTH: 15
<212> TYPE: DNA
<213> ORGANISM: Homo sapiens

<400> SEQUENCE: 53
agctattgga tgagc                                                      15

<210> SEQ ID NO 54
<211> LENGTH: 5
<212> TYPE: PRT
<213> ORGANISM: Homo sapiens

<400> SEQUENCE: 54

```
Ser Tyr Trp Met Ser
 1               5
```

<210> SEQ ID NO 55
<211> LENGTH: 27
<212> TYPE: DNA
<213> ORGANISM: Homo sapiens

<400> SEQUENCE: 55
caacagtata atagttaccc tcccacc                                    27

<210> SEQ ID NO 56
<211> LENGTH: 9
<212> TYPE: PRT
<213> ORGANISM: Homo sapiens

<400> SEQUENCE: 56

Gln Gln Tyr Asn Ser Tyr Pro Pro Thr
1               5

<210> SEQ ID NO 57
<211> LENGTH: 21
<212> TYPE: DNA
<213> ORGANISM: Homo sapiens

<400> SEQUENCE: 57
gctgcatcca gtttgcaaag t                                          21

<210> SEQ ID NO 58
<211> LENGTH: 7
<212> TYPE: PRT
<213> ORGANISM: Homo sapiens

<400> SEQUENCE: 58

Ala Ala Ser Ser Leu Gln Ser
1               5

<210> SEQ ID NO 59
<211> LENGTH: 33
<212> TYPE: DNA
<213> ORGANISM: Homo sapiens

<400> SEQUENCE: 59
cgggcgagtc agggtattag cagctggtta gcc                             33

<210> SEQ ID NO 60
<211> LENGTH: 11
<212> TYPE: PRT
<213> ORGANISM: Homo sapiens

<400> SEQUENCE: 60

Arg Ala Ser Gln Gly Ile Ser Ser Trp Leu Ala
1               5                   10

<210> SEQ ID NO 61
<211> LENGTH: 36
<212> TYPE: DNA
<213> ORGANISM: Homo sapiens

<400> SEQUENCE: 61
gagggtaatc gtagccacta tatacccttt gcctac                          36

<210> SEQ ID NO 62
<211> LENGTH: 12
<212> TYPE: PRT
<213> ORGANISM: Homo sapiens

<400> SEQUENCE: 62

Glu Gly Asn Arg Ser His Tyr Ile Pro Phe Ala Tyr
1               5                   10

<210> SEQ ID NO 63

```
<211> LENGTH: 51
<212> TYPE: DNA
<213> ORGANISM: Homo sapiens

<400> SEQUENCE: 63
gttatatggt atgatggaag taataaatac tatgcagact ccgtgaaggg c          51

<210> SEQ ID NO 64
<211> LENGTH: 17
<212> TYPE: PRT
<213> ORGANISM: Homo sapiens

<400> SEQUENCE: 64

Val Ile Trp Tyr Asp Gly Ser Asn Lys Tyr Tyr Ala Asp Ser Val Lys
 1               5                  10                  15

Gly

<210> SEQ ID NO 65
<211> LENGTH: 15
<212> TYPE: DNA
<213> ORGANISM: Homo sapiens

<400> SEQUENCE: 65
agctatggca tgcac                                                  15

<210> SEQ ID NO 66
<211> LENGTH: 5
<212> TYPE: PRT
<213> ORGANISM: Homo sapiens

<400> SEQUENCE: 66

Ser Tyr Gly Met His
 1               5

<210> SEQ ID NO 67
<211> LENGTH: 27
<212> TYPE: DNA
<213> ORGANISM: Homo sapiens

<400> SEQUENCE: 67
caacagtata atagttaccc gcgcact                                     27

<210> SEQ ID NO 68
<211> LENGTH: 9
<212> TYPE: PRT
<213> ORGANISM: Homo sapiens

<400> SEQUENCE: 68

Gln Gln Tyr Asn Ser Tyr Pro Arg Thr
 1               5

<210> SEQ ID NO 69
<211> LENGTH: 21
<212> TYPE: DNA
<213> ORGANISM: Homo sapiens

<400> SEQUENCE: 69
gctgcatcca gtttgcaaag t                                           21

<210> SEQ ID NO 70
<211> LENGTH: 7
<212> TYPE: PRT
<213> ORGANISM: Homo sapiens
```

-continued

```
<400> SEQUENCE: 70

Ala Ala Ser Ser Leu Gln Ser
 1               5

<210> SEQ ID NO 71
<211> LENGTH: 33
<212> TYPE: DNA
<213> ORGANISM: Homo sapiens

<400> SEQUENCE: 71
cgggcgagtc agggtattag cagctggtta gcc                                      33

<210> SEQ ID NO 72
<211> LENGTH: 11
<212> TYPE: PRT
<213> ORGANISM: Homo sapiens

<400> SEQUENCE: 72

Arg Ala Ser Gln Gly Ile Ser Ser Trp Leu Ala
 1               5                  10
```

HUMAN MONOCLONAL ANTIBODIES AGAINST BACILLUS ANTHRACIS PROTECTIVE ANTIGEN

BACKGROUND OF THE INVENTION

Anthrax (*Bacillus anthracis*) is primarily a disease of domesticated and wild animals, particularly herbivorous animals, such as cattle, sheep, horses, mules, and goats. Although natural anthrax infection in humans is rare (risk of infection through contact with diseased animals is about 1/100,000), it poses a very real threat from bioterrorism. The bacteria form hardy spores which are heat resistant and can survive for decades under crude conditions. Although cutaneous anthrax is more readily treatable, inhalation anthrax typically results in an abrupt catastrophic illness having a mortality rate of greater than 80% in 2-4 days. The ease by which the disease can be spread due to the stability of the spores was made evident from the five deaths that occurred in the U.S. in 2002. If anthrax spores were spread through an act of terrorism, the event would likely be undiscoverable until large numbers of people sought treatment or died. Current therapies, including antibiotics and vaccines, cannot help most of these victims.

The current model of anthrax infection teaches that after gemination of spores, the actively growing bacterial cells produce a capsule containing poly-D-glutamate polypeptide, which protects the bacteria against the bactericidal components of serum and phagocytes and phagocytic engulfment. The capsule is more important during the establishment of the infection than in the terminal phases of the disease, which are mediated by the anthrax toxin. The toxin, which is responsible for the disease etiology, is composed of protective antigen (PA), lethal factor (LF) and edema factor (EF). The EF is a calcium-calmodulin-dependent adenylate cyclase believed to cause the edema associated with anthrax infection and to prevent immune cells from ingesting and degrading the bacteria. The LF is a cell-type specific metalloprotease that cleaves mitogen-activated protein kinase-kinases and several peptide hormones. It causes macrophage cell death and release of toxic substances (e.g., those associated with septic shock such as TNF-$\alpha$ and IL-1). LF is the major virulence factor associated with anthrax toxicity and is responsible for systemic shock and death.

None of the toxin components are pathogenic alone, and EF and LF require PA to exert their toxic effects inside a host cell. During infection, an 83 kDa protective antigen PA83 protein secreted from rapidly growing *B. anthracis* binds to the host's cell surface via the anthrax toxin receptor (ATR) (Bradley et al, 2001, Nature 414:225-229). Cleavage of the PA83 by a membrane-bound furin and/or a furin-like protease releases an amino-terminal 20 kDa PA fragment, resulting in receptor-bound 63 kDa PA. Oligomerization of PA63 into a heptameric ring forms a high-affinity binding site recognized by the amino termini of both LF and EF. Endocytosis of the receptor-toxin complex into acidic endosomes elicits a conformational change in PA63 whereby LF or EF is released into the endosome. Lysosomal acidification and subsequent receptor release facilitates irreversible membrane insertion of the oligomeric PA63 pore. The pore formed by PA63 permits transport of LF and EF into the cytoplasm where they can elicit their respective toxicities.

Several modes of interrupting PA function have been explored in order to develop treatments against anthrax. Soluble ATR (sATR) introduced into media containing ATR-bearing cells (e.g., macrophages), causes PA to bind to the sATR instead of the receptor on the cell surface (Bradley et al., 2003, Biochem. Pharmacol. 65: 309-314) suggesting that ATR may be useful in the design of anthrax treatments. It has also been shown that mutant forms of PA called dominant negative inhibitors (DNIs) permit formation of the heptameric complex when mixed with native PA, which was unable to inject the EF and LF into the cell in both cell culture and rodent models (Sellman et al., 2001, Science 292: 695-697). Monoclonal antibodies generated against the PA may lessen the symptoms of infection as well as provide prophylaxis. An antibody may block the binding of PA to its receptor on the surface of the cell and/or it may block the EF or LF from binding to the PA. Either of these methods could prevent toxin from entering the cells and causing damage. While antibiotics alone may control bacterial expansion, they do nothing to neutralize the effects of the toxin. In addition, it may be possible to engineer resistance into the bacteria thereby rendering the antibiotic useless.

Anthrax vaccine (AVA), which contains PA as the primary immunogenic component, may confer protection against the disease. However, there are several drawbacks to using AVAs. The immunization schedule (e.g., six initial doses followed by yearly boosters) does not generate strong immunological memory. Also, a lack of standardization of the level of antigen results in a high degree of variability in efficacy on a lot-lot basis. Furthermore, since the vaccine is a cell-free culture media filtrate, which contains several cellular components, it may contribute to a high incidence of local and systemic reactions. In a prophylactic use of polyclonal antibodies generated in response to the vaccine, antibodies to PA have been shown to prevent disease following exposure to anthrax. Development of human scFv screened from a naïve single-chain Fv phagemid library for antibodies that bind PA have been described (Cirino et al., 1999, Infection and Immunity 67: 2957-2963). These PA binding agents were selected against purified PA83 based on their ability to inhibit receptor-mediated binding of PA to cells. However, since these immunological agents are not complete antibodies, their use in treatments is limited by a decreased half-life and lower avidity, which may require much higher dosages, particularly in prophylactic treatments.

Monoclonal antibodies have advantages over antibiotics, but also which can be used to augment antibody efficacy. For treatment of active pulmonary disease, antibiotics will not neutralize the preformed and released toxin that is causing the pathology, whereas antibodies can neutralize additional toxin before it can contribute further to the inflammatory cascade. For prophylactic treatment, the duration of required antibiotic prophylaxis is 60 days, which can be difficult to follow. Furthermore, this time span may be covered by a single injection of antibody. Moreover, in true exposures, antibiotics can interfere with the development of a protective immune response so that there is no protection afforded after dosing is terminated.

Accordingly, there is a need for improved therapies for treating anthrax infection, particularly antibodies against *B. anthracis* protective antigen, which will be well tolerated by the immune system and capable of prophylactic, post-exposure prophylactic, and therapeutic uses.

SUMMARY OF THE INVENTION

The present invention provides isolated human monoclonal antibodies, which bind to the protective antigen of *Bacillus anthracis* (anthrax) thereby inhibiting its biological activity, as well as derivatives (e.g., immunoconjugates, bispecific molecules and single chain fragments (ScFv) and other therapeutic compositions containing such antibodies, alone or in combination with additional therapeutic agents. Also provided are methods and compositions for treating and preventing anthrax infection using the antibodies of the invention.

Antibodies of the present invention provide an improved means for treating and preventing anthrax infection attributable in part to the antibodies' ability to effectively neutralize protective antigen activity and to the antibodies' fully human composition, which makes them significantly less immunogenic and more therapeutically effective and useful when administered to human patients than other protective antigen antibodies previously generated (e.g., murine and humanized antibodies).

Thus, in one aspect, the invention provides fully human antibodies that bind to *Bacillus anthracis* protective antigen with an apparent affinity of at least $10^7$ M$^{-1}$ and neutralize a *Bacillus anthracis* toxin at an $ED_{50}$ of 5 µg/ml or less in a toxin neturalization assay.

In another aspect, the invention provides neutralizing human monoclonal antibodies against anthrax protective antigen, which have one or more of the following characteristics:
  (1) requires binding to Fc receptor for neutralization activity;
  (2) exhibits higher affinity for PA 63 over PA 83;
  (3) exhibits one or more characteristics selected from:
    (a) does not bind PA 83 at 1 µg/ml, $OD_{405\ nm}$ 0.2 or less according to standard ELISA,
    (b) does not block anthrax lethal factor or edema factor from binding protective antigen in a competitive binding assay;
  (4) does not compete with an anti-PA antibody selected from murine 1G3, murine 2D5 and murine 14B7 in binding to PA 63.

In a particular embodiment, the antibody has a human heavy chain variable region and a human light chain variable region where the sequences of the human heavy chain variable region and the human light chain variable region respectively comprise the sequences selected from SEQ ID NOs: 2 and 4, SEQ ID NOs: 2 and 6, SEQ ID NOs: 8 and 10, SEQ ID NOs: 12 and 14, or SEQ ID NOs: 16 and 18, and include conservative sequence modifications thereof.

In another embodiment, the antibody has a human heavy chain variable region containing FR1, CDR1, FR2, CDR2, FR3, CDR3 and FR4 sequences and a human light chain variable region comprising FR1, CDR1, FR2, CDR2, FR3, CDR3 and FR4 sequences, where the human heavy chain variable region CDR3 sequence is selected from SEQ ID NOs: 20, 38, 50 and 62, and conservative modifications thereof; and the human light chain variable region CDR3 sequence is selected from SEQ ID NOs: 26, 32, 44, 56 and 68, and conservative modifications thereof.

In yet another embodiment, particular human antibodies of the invention include those which comprise a CDR domain having a human heavy and light chain CDR1 region, a human heavy and light chain CDR2 region, and a human heavy and light chain CDR3 region, which comprise an amino acid sequence at least 80% homologous, preferably 85% homologous, more preferably 90%, 95%, 98%, or 99% homologous to the amino acid sequences of the CDR1, CDR2, and CDR3 regions shown in FIGS. 1-9.

In still another embodiment, the antibody has a human heavy chain variable region and a human light chain variable region, where the human heavy chain variable region contains an amino acid sequence selected from SEQ ID NOs: 2, 8, 12 and 16, and sequences that are at least 80% homologous to SEQ ID NOs: 2, 8, 12 and 16, and the human light chain variable region contains an amino acid sequence selected from SEQ ID NOs: 4, 6, 10, 14 and 18, and sequences that are at least 80% homologous to SEQ ID NOs: 4, 6, 10, 14 and 18.

A particular therapeutic antibody of the present invention includes human monoclonal antibody (HuMab) 5E8 and functionally equivalent antibodies which (a) are encoded by human heavy chain and human light chain nucleic acids comprising nucleotide sequences in their variable regions as set forth in SEQ ID NO:1 and SEQ ID NO:3, respectively, and conservative sequence modifications thereof, or (b) include heavy chain and light chain variable regions which comprise the amino acid sequences shown in SEQ ID NO:2 and SEQ ID NO:4, respectively, and conservative sequence modifications thereof. In another embodiment, the light chain variable region of HuMab 5E8 comprises a nucleotide sequence and amino acid sequence as set forth in SEQ ID NOs: 5 and 6, respectively, including conservative modifications thereof.

Another particular therapeutic antibody of the present invention includes human monoclonal antibody 2D5 and functionally equivalent antibodies which (a) are encoded by human heavy chain and human light chain nucleic acids comprising nucleotide sequences in their variable regions as set forth in SEQ ID NO:7 and SEQ ID NO:9, respectively, and conservative sequence modifications thereof, or (b) include heavy chain and light chain variable regions which comprise the amino acid sequences shown in SEQ ID NO:8 and SEQ ID NO:10, respectively, and conservative sequence modifications thereof.

Yet another particular therapeutic antibody of the present invention includes human monoclonal antibody 2H4 and functionally equivalent antibodies which (a) are encoded by human heavy chain and human light chain nucleic acids comprising nucleotide sequences in their variable regions as set forth in SEQ ID NO:11 and SEQ ID NO: 13, respectively, and conservative sequence modifications thereof, or (b) include heavy chain and light chain variable regions which comprise the amino acid sequences shown in SEQ ID NO:12 and SEQ ID NO:14, respectively, and conservative sequence modifications thereof.

Still another particular therapeutic antibody of the present invention includes human monoclonal antibody 5D5 and functionally equivalent antibodies which (a) are encoded by human heavy chain and human light chain nucleic acids comprising nucleotide sequences in their variable regions as set forth in SEQ ID NO:15 and SEQ ID NO:17, respectively, and conservative sequence modifications thereof, or (b) include heavy chain and light chain variable regions which comprise the amino acid sequences shown in SEQ ID NO:16 and SEQ ID NO:18, respectively, and conservative sequence modifications thereof.

The invention further encompasses antibodies that bind to an epitope on anthrax protective antigen defined by antibody 5E8, 2D5, 2H4 or 5D5, and/or which compete for binding to protective antigen with antibody 5E8, 2D5, 2H4 or 5D5, or which have other functional binding characteristics exhibited by antibody 5E8, 2D5, 2H4 or 5D5. Such antibodies include those which specifically bind to protective antigen (e.g., no cross-reactivity with cell-surface antigens) and exhibit toxin neutralizing activity.

In yet another aspect, the invention provides nucleic acid molecules encoding human anti-PA antibodies and portions thereof (e.g., variable regions thereof), as well as recombinant expression vectors which include the nucleic acids of the invention, and host cells transfected with such vectors. Methods of producing the antibodies by culturing these host cells are also encompassed by the invention. Particular nucleic acids encoding antibodies of the invention include the nucleotide sequences for antibodies 5E8, 2D5, 2H4 and 5D5.

In another aspect, the invention provides a transgenic non-human animal having a genome comprising a human heavy chain transgene or transchromosome and a human light chain transgene or transchromosome, which express human monoclonal antibodies that bind to protective antigen. In a particular embodiment, the transgenic non-human animal is a transgenic mouse (also referred to herein as a "HuMAb mouse®").

In yet another aspect, the invention provides isolated B-cells from a transgenic non-human animal as described, e.g., a transgenic mouse, which expresses human anti-PA antibodies. The isolated B-cells can then be immortalized by fusion to an immortalized cell to provide a source (e.g., a hybridoma) of human anti-PA antibodies. Such hybridomas (i.e., which produce human anti-protective antigen antibodies) are also included within the scope of the invention.

As exemplified herein, human antibodies of the invention can be obtained directly from hybridomas which express the antibody, or can be cloned and recombinantly expressed in a host cell (e.g., a CHO cell or a lymphocytic cell). Accordingly, in another aspect, the present invention provides methods for producing human monoclonal antibodies which bind to anthrax protective antigen by immunizing with *B. anthracis* protective antigen, or a cell expressing *B. anthracis* protective antigen, a transgenic non-human animal having a genome containing a human heavy chain transgene and a human light chain transgene, such that antibodies are produced by B cells of the animal, isolating the B cells, and fusing the B cells with myeloma cells to form immortal hybridoma cells that secrete the antibody. In one embodiment, the method includes immunizing a HuMAb Mouse® with a purified or enriched preparation of anthrax protective antigen and/or cells expressing anthrax protective antigen.

In yet another aspect, human anti-PA antibodies of the invention are derivatized, linked to, or co-expressed with another functional molecule, e.g., another peptide or protein (e.g., a Fab' fragment). For example, an antibody or antigen-binding portion of the invention can be functionally linked (e.g., by chemical coupling, genetic fusion, noncovalent association or otherwise) to one or more other molecular entities, such as another antibody to produce a bispecific or a multispecific antibody. Accordingly, the present invention encompasses a large variety of antibody conjugates, bispecific and multispecific molecules, and fusion proteins, all of which bind to anthrax protective antigen, and can be used to target the anthrax protective antigen to particular cells.

In yet another aspect, the present invention provides a method for detecting in vitro or in vivo the presence of anthrax protective antigen in a sample, e.g., for diagnosing anthrax infection. In one embodiment, this is achieved by contacting a sample to be tested, optionally along with a control sample, with a human monoclonal antibody of the invention (or an antigen-binding portion thereof) under conditions that allow for formation of a complex between the antibody and protective antigen followed by detection of the complex formed (e.g., using an ELISA). When using a control sample along with the test sample, complex is detected in both samples and any statistically significant difference in the formation of complexes between the samples is indicative the presence of protective antigen in the test sample.

In another aspect, the present invention provides methods of screening for an antibody against anthrax protective antigen by the sequential steps of selecting one or more antibodies which neutralizes anthrax toxin in a toxin neutralization assay, followed by selecting an antibody which has an $ED_{50}$ of 0.1 µg/ml or less, where an antigen-antibody binding affinity assay is not used as a selection criterion prior to either step.

In another aspect, the present invention provides therapeutic and diagnostic compositions comprising one or more human anti-PA antibodies together with a carrier. In a particular embodiment, the composition further includes one or more additional therapeutic agents, such as a protective antigen vaccine or a second antibody against anthrax bacteria, spores, protective antigen, lethal factor or edema factor, or a Fab, $F(ab')_2$, Fv or single chain Fv fragment of the second antibody.

In another aspect, the invention provides methods of in vivo treatment and prevention of anthrax by administering human antibodies of the present invention to patients (e.g., human subjects) at therapeutically effective dosages using any suitable route of administration known in the art for antibody-based clinical products, e.g., SC injection and intravenous.

In a particular embodiment, the invention provides methods for treating or preventing anthrax in a patient in need of such treatment by administering a neutralizing antibody against anthrax protective antigen, having the characteristics that (1) it requires binding to Fc receptor for neutralization activity, (2) exhibits higher affinity for PA 63 over PA 83, (3) exhibits one or more of (a) does not bind PA 83 at 1 µg/ml, $OD_{405\,nm}$ 0.2 or less according to standard ELISA, (b) does not block anthrax lethal factor or edema factor from binding protective antigen in a competitive binding assay (e.g., see Little, 1996), and (4) does not compete with an anti-PA antibody selected from murine 1G3, murine 2D5 and murine 14B7 in binding to PA 63, in a dosage from 0.1 mg/kg to 100 mg/kg. In another particular embodiment of the invention, patients infected with anthrax and exhibiting signs and/or symptoms of anthrax disease can be treated with an antibody of the invention.

In a particular embodiment, human antibodies of the invention are co-administered with one or more additional therapeutic agents, e.g., an antibiotic, a protective antigen vaccine or antibodies against anthrax bacteria, spores, protective antigen, lethal factor or edema factor. Such additional agents can be co-administered simultaneously with administration of an antibody of the invention (e.g., in a single composition or separately) or administered before or after administration of the anti-PA antibody.

Other features and advantages of the instant invention will be made apparent from the following detailed description and examples which should not be construed as limiting. The contents of all references, patents and published patent applications cited throughout this application are expressly incorporated herein by reference.

BRIEF DESCRIPTION OF THE DRAWINGS

FIG. 1 shows the nucleotide sequence (SEQ ID NO: 1) and corresponding amino acid sequence (SEQ ID NO: 2) of the $V_H$-region from HuMab 5E8. CDR regions are indicated.

FIG. 2 shows the nucleotide sequence (SEQ ID NO: 3) and corresponding amino acid sequence (SEQ ID NO: 4) of the $V_L$-region from HuMab 5E8 (major). CDR regions are indicated.

FIG. 3 shows the nucleotide sequence (SEQ ID NO: 5) and corresponding amino acid sequence (SEQ ID NO: 6) of the $V_H$-region from HuMab 5E8 (minor). CDR regions are indicated.

FIG. 4 shows the nucleotide sequence (SEQ ID NO: 9) and corresponding amino acid sequence (SEQ ID NO: 10) of the $V_H$-region from HuMab 2D5. CDR regions are indicated.

FIG. 5 shows the nucleotide sequence (SEQ ID NO: 11) and corresponding amino acid sequence (SEQ ID NO: 12) of the $V_L$-region from HuMab 2D5. CDR regions are indicated.

FIG. 6 shows the nucleotide sequence (SEQ ID NO: 13) and corresponding amino acid sequence (SEQ ID NO: 14) of the $V_H$-region from HuMab 2H4. CDR regions are indicated.

FIG. 7 shows the nucleotide sequence (SEQ ID NO: 15) and corresponding amino acid sequence (SEQ ID NO: 16) of the $V_L$-region from HuMab 2H4. CDR regions are indicated.

FIG. 8 shows the nucleotide sequence (SEQ ID NO: 17) and corresponding amino acid sequence (SEQ ID NO: 18) of the $V_H$-region from HuMab 5D5-2E10. CDR regions are indicated.

FIG. 9 shows the nucleotide sequence (SEQ ID NO: 19) and corresponding amino acid sequence (SEQ ID NO: 20) of the $V_L$-region from HuMab 5D5-2E10. CDR regions are indicated.

Figure 11:
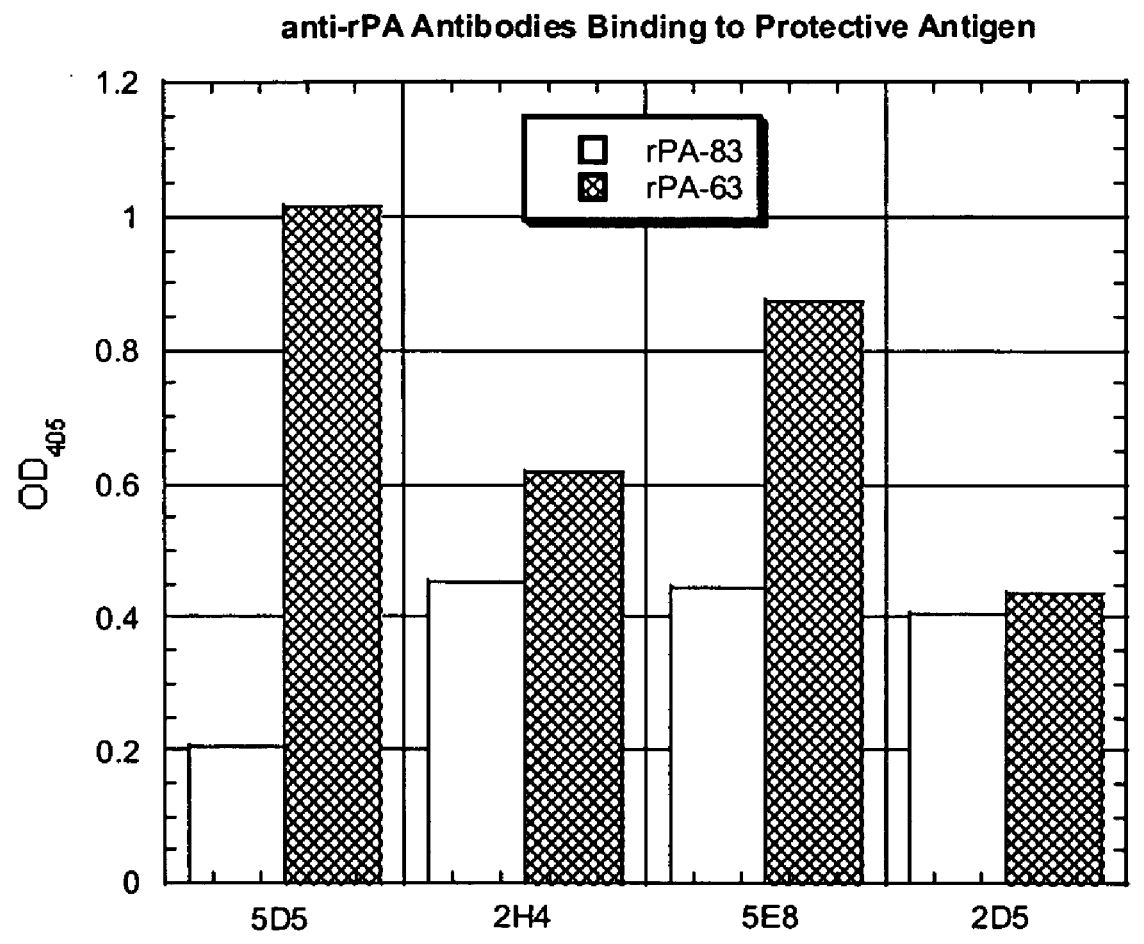

FIG. 11 is a graph showing anti-PA antibodies binding by ELISA to full-length protective anitgen (83 kD; white bars) and cleaved protective antigen (63 kD; hatched bars).

FIG. 15 is a graph showing a competitive binding assay between HuMAb 5E8 and 3 murine mAbs using PA 63 standard ELISA.

DETAILED DESCRIPTION OF THE INVENTION

Figure 10:
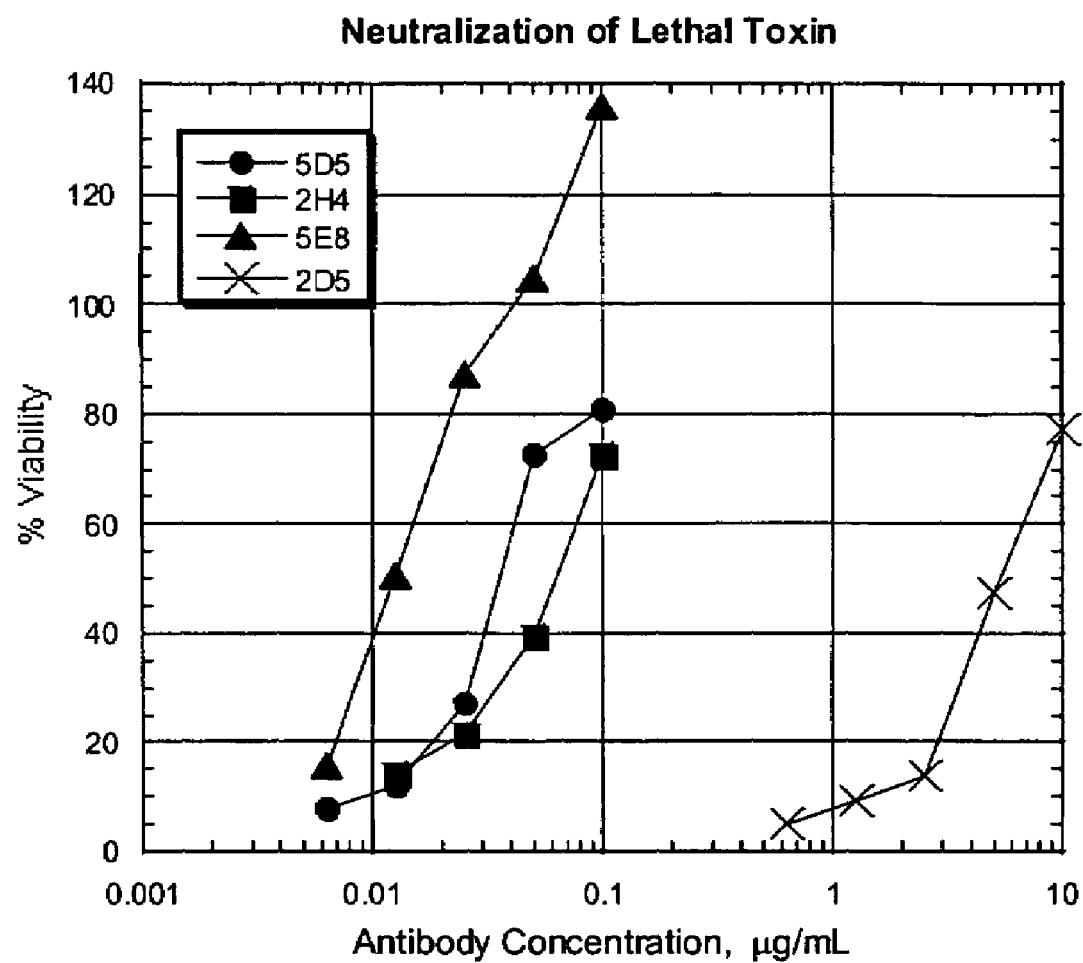
FIG. 10 is a graph showing neutralization of *B. anthracis* lethal toxin by four different human anti-PA antibodies.
Figure 12:
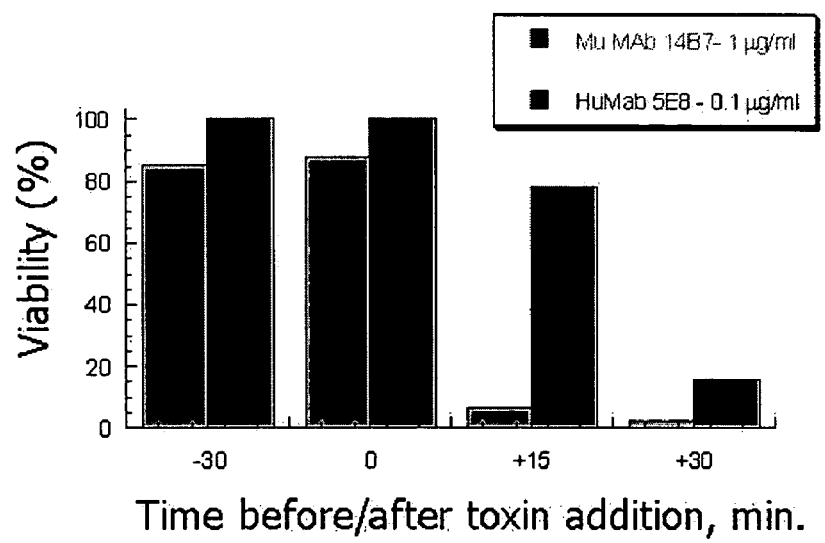
FIG. 12 is a graph showing a kinetic analysis of neutralization of *B. anthracis* lethal toxin by HuMAb 5E8 and murine mAb 14B7.

The present invention provides novel anti-PA antibodies and improved antibody-based therapies for treating and diagnosing anthrax (*B. anthracis*). Methods of the invention employ isolated human monoclonal antibodies, or antigen binding portions thereof, which bind to anthrax protective antigen and inhibit the functions of anthrax protective antigen, edema factor and/or lethal factor, which methods are useful in human therapy.

Antibodies of the invention can be full-length (e.g., an IgG1 or IgG3 antibody) or can include only an antigen-binding portion (e.g., a Fab, F(ab')$_2$, Fv or a single chain Fv fragment). In one embodiment, the human antibodies are produced in a non-human transgenic animal, e.g., a transgenic mouse, capable of producing multiple isotypes of human monoclonal antibodies to anthrax PA (e.g., IgG, IgA and/or IgE) by undergoing V-D-J recombination and isotype switching. Accordingly, particular aspects of the invention include not only antibodies, antibody fragments, and pharmaceutical compositions thereof, but also non-human transgenic animals, B-cells and hybridomas which produce monoclonal antibodies. Methods of using the antibodies of the invention to detect anthrax PA in a biological sample, are also encompassed by the invention. Methods for using the antibodies of the invention to block or inhibit anthrax PA-induced biology, e.g., toxin-associated functions, are also provided and are useful in the treatment or prevention of anthrax infection.

In order that the present invention may be more readily understood, certain terms are first defined below, and additional definitions are set forth throughout the Detailed description.

As used herein, "protective antigen" and "PA" refer to the protective antigen protein produced by the bacterium *Bacillus antracis* (anthrax), and include any variants, isoforms and species homologs of anthrax protective antigen, which may be naturally expressed by the bacterium or recombinantly, expressed [see Welkos et al., Gene 69: 287-300 (1988)]. The terms "protective antigen" and "PA" refer to both the 83 kD (PA83) and 63 kD (PA63) forms of anthrax protective antigen, unless a term is specifically limited to one form or the other.

In one embodiment, an anti-PA antibody of the invention "neutralizes" an anthrax toxin (i.e., lethal factor or edema factor). As used herein, "neutralizes" and grammatical variations thereof, refer to an activity of an antibody of the present invention, which activity prevents entry or translocation of EF or LF into a cell susceptible to anthrax infection upon binding of the antibody to the anthrax PA. Although not intending to be limited by any particular mechanism of action, binding of an antibody of the invention to anthrax PA can result in prevention of toxin translocation into a cell's cytoplasm at a number of different points during the infection process, e.g., (1) binding of anthrax PA to ATR on a cell, (2) cleavage of the PA83 to the PA63 form, (3) formation of a heptamer comprising seven PA63 units, and (4) binding of the toxin to, or otherwise associating with, the heptamer. An antibody of the invention can neutralize anthrax toxin by inhibiting or blocking any one or more of the different points during the infection process through binding to anthrax PA.

In vitro assays for determining whether a therapeutic compound, such as a human antibody of the invention, can neutralize anthrax toxin are well known in the art. Such activity of an antibody of the invention can be determined, e.g., by a toxin neutralization assay (TNA) (see, e.g., Little et al., 1990, Infection and Immunity 58: 1606-1613, which describes use of a toxin-sensitive macrophage cell line J774A. 1 that is exposed to mixtures of anthrax LF and PA in the presence of an anti-PA antibody where antibody-mediated neutralization of the toxin results in increased survival of the macrophages; Little et al., 1994, Biochem. Biophys. Res. Commun. 199: 676-82; and Little et al., 1996, Microbiology 142: 707-715). In performing a TNA to determine the effectiveness of an antibody of the invention, the effective dose (ED) for an antibody capable of achieving 50% (ED$_{50}$) cell viability is measured. Anti-PA antibodies useful in the present invention neutralize anthrax toxin in concentrations of less than 5 µg/ml, more preferably less than 1 µg/ml, and most preferably less than 0.1 µg/ml. Thus, antibodies of the invention have an ED$_{50}$ of from about 0.001 to 5 µg/ml, preferably 1 µg/ml or less, and most preferably 0.1 µg/ml or less, as measured by TNA.

The term "antibody" as referred to herein includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to bind to an antigen (e.g., B. anthracis protective antigen). It has been shown that the antigen-binding function of an antibody can be performed by fragments of a full-length antibody. The term "binding fragments," which is encompassed within the term "antigen-binding portion" of an antibody, includes (i) a Fab fragment, a monovalent fragment consisting of the $V_L$, $V_H$, $C_L$ and $C_H$, domains; (ii) a F(ab')$_2$ fragment, a bivalent fragment comprising two Fab fragments linked by a disulfide bridge at the hinge region; (iii) a Fd fragment consisting of the $V_H$ and $C_{H1}$, domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "epitope" means a protein determinant capable of specific binding to an antibody. Epitopes typically consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "bispecific molecule" is intended to include any agent, e.g., a protein, peptide, or protein or peptide complex, which has two different binding specificities. For example, the molecule may bind to, or interact with, (a) a cell surface antigen and (b) another anti-PA antibody. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) another anti-PA antibody, and (c) at least one other component. Accordingly, the invention includes, but is not limited to, bispecific, trispecific, tetraspecific, and other multispecific molecules which are directed to cell surface antigens, such as B. anthracis protective antigen, and to other targets, such as another anti-PA antibody.

The term "bispecific antibodies" also includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

As used herein, the term "heteroantibodies" refers to two or more antibodies, antibody binding fragments (e.g., Fab), derivatives therefrom, or antigen binding regions linked together, at least two of which have different specificities. These different specificities include a binding specificity for another anthrax antigen.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody", as used herein, is intended to include all human antibodies that are prepared, expressed, created or isolated by recombinant means, such as (a) antibodies isolated from an animal (e.g., a mouse) that is transgenic for human immunoglobulin genes (described further in Section I, below), (b) antibodies expressed using a recombinant expression vector transfected into a host cell, (c) antibodies isolated from a recombinant, combinatorial human antibody library, and (c) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, a "heterohybrid antibody" refers to an antibody having a light and heavy chains of different organismal origins. For example, an antibody having a human heavy chain associated with a murine light chain is a heterohybrid antibody. Examples of heterohybrid antibodies include chimeric and humanized antibodies, discussed supra.

An "isolated antibody," as used herein, is intended to refer to an antibody which is substantially free of other antibodies having different antigenic specificities (e.g., an isolated antibody that binds to protective antigen is substantially free of antibodies that bind antigens other than protective antigen). An isolated antibody that binds to an epitope, isoform or variant of anthrax protective antigen may, however, have cross-reactivity to other related antigens, e.g., from other bacterial species (e.g., protective antigen species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding" refers to an anti-PA antibody of the present invention binding anthrax protective antigen. Typically, the antibody binds with an affinity of at least about $1\times10^7$ $M^{-1}$, and binds to the protective antigen with an affinity that is at least two-fold greater than its affinity for binding to a non-specific antigen (e.g., BSA, casein) other than the protective antigen or a closely-related antigen. The phrases "an antibody recognizing protective antigen" and "an antibody specific for protective antigen" are used interchangeably herein with the term "an antibody which binds specifically to protective antigen".

As used herein, the term "high affinity" for an IgG antibody refers to a binding affinity of at least about $10^7$ $M^{-1}$, preferably at least about $10^8$ $M^{-1}$, more preferably at least about $10^9$ $M^{-1}$, $10^{10}$ $M^{-1}$, $10^{11}$ $M^{-1}$ or greater, e.g., up to $10^3$ $M^{-1}$ or greater. However, "high affinity" binding can vary for other antibody isotypes. For example, "high affinity" binding for an IgM isotype refers to a binding affinity of at least about $1\times10^7M^{-1}$.

The term "$K_{assoc}$" or "$K_a$", as used herein, is intended to refer to the association constant of a particular antibody-antigen interaction.

The term "$K_{dis}$" or "$K_d$", as used herein, is intended to refer to the dissociation constant of a particular antibody-antigen interaction.

As used herein, "isotype" refers to the antibody class (e.g., IgM or IgG1) that is encoded by heavy chain constant region genes. An isolated human antibody of the invention can be any antibody isotype, e.g., IgG1, IgG2, IgG3, IgG4, IgM, IgA1, IgA2, IgAsec, IgD, and IgE.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ (δ-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a μ switch region, will be 5' (i.e., upstream) of the construct region to be deleted during the switch recombination. The "switch acceptor" region will be between the construct-region to be deleted and the replacement constant region (e.g., γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., $V_H$, $V_L$, CDR3) that bind to protective antigen, refers to a nucleic acid molecule in which the nucleotide sequences encoding the antibody or antibody portion are free of other nucleotide sequences encoding antibodies or antibody portions that bind antigens other than protective antigen, which other sequences may naturally flank the nucleic acid in human genomic DNA. In one embodiment, the human anti-PA antibody, or portion thereof, has the nucleotide and amino acid sequence of 5E8 (and 5E8'), 2D5, 2H4, 5D5, or heavy chain ($V_H$) variable regions having the nucleotide and amino acid sequences, respectively, shown in SEQ ID NOs: 1 and 2, 7 and 8, 11 and 12, and 15 and 16, or light chain ($V_L$) variable regions having the nucleotide and amino acid sequences, respectively, shown in SEQ ID NOs: 3 and 4, 5 and 6, 9 and 10, 13 and 14, and 17 and 18. Those having ordinary skill in the art shall appreciate that the antibodies 5E8 and 5E8' have the same heavy chain, while differing in their light chain, where 5E8 has a light chain ($V_{L\ major}$) variable region that has the nucleotide and amino acid sequences, respectively, shown in SEQ ID NOs: 3 and 4 and 5E8' has a light chain ($V_{L\ minor}$) variable region that has the nucleotide and amino acid sequences, respectively, shown in SEQ ID NOs: 5 and 6. Both of these antibodies from the 5E8 hybridoma bind to anthrax protective antigen and neutralize anthrax toxin in the TNA.

As disclosed and claimed herein, the sequences set forth in SEQ ID NOs: 1-72 include "conservative sequence modifications", i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into SEQ ID NOs: 1-72 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-PA antibody is preferably replaced with another amino acid residue from the same side chain family.

Alternatively, in another embodiment, mutations can be introduced randomly along all or part of an anti-PA antibody coding sequence, such as by saturation mutagenesis, and the resulting modified anti-PA antibodies can be screened for binding activity.

Accordingly, antibodies encoded by the (heavy and light chain variable region) nucleotide sequences disclosed herein and/or containing the (heavy and light chain variable region) amino acid sequences disclosed herein (i.e., SEQ ID NOs: 1-18) include substantially similar antibodies encoded by or containing similar sequences which have been conservatively modified. Further discussion as to how such substantially similar antibodies can be generated based on the partial (i.e., heavy and light chain variable regions) sequences disclosed herein as SEQ ID NOs: 1-18 is provided below.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at www.gcg.com), using a NWSgap-dna.CMP matrix and a gap weight of 40, 50, 60, 70, or 80 and a length weight of 1, 2, 3, 4, 5, or 6. The percent identity between two nucleotide or amino acid sequences can also determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley Interscience, New York (1987).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells and lymphocytic cells.

Various aspects of the invention are described in further detail in the following subsections.

I. Production of Human Antibodies to B. anthracis Protective Antigen

The monoclonal antibodies (MAbs) of the invention can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

In a preferred embodiment, human monoclonal antibodies directed against protective antigen can be generated using transgenic mice carrying parts of the human immune system rather than the mouse system. These transgenic mice, referred to herein as "HuMAb" mice, contain a human immunoglobulin gene miniloci that encodes unrearranged human heavy (μ and γ) and κ light chain immunoglobulin sequences, together with targeted mutations that inactivate the endogenous μ and κ chain loci (Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGK monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. Vol. 13: 65-93, and Harding, F. and Lonberg, N. (1995) Ann. N.Y. Acad. Sci 764:536-546). The preparation of HuMAb mice is described in detail Section II below and in Taylor, L. et al. (1992) Nucleic Acids Research 20:6287-6295; Chen, J. et al. (1993) International Immunology 5: 647-656; Tuaillon et al. (1993) Proc. Natl. Acad. Sci USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Lonberg et al., (1994) Nature 368(6474): 856-859; Lonberg, N. (1994) Handbook of Experimental Pharmacology 113:49-101; Taylor, L. et al. (1994) International Immunology 6: 579-591; Lonberg, N. and Huszar, D. (1995) Intern. Rev. Immunol. Vol. 13: 65-93; Harding, F. and Lonberg, N. (1995) Ann. N.Y. Acad. Sci 764:536-546; Fishwild, D. et al. (1996) Nature Biotechnology 14: 845-851, the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992, the disclosures of all of which are hereby incorporated by reference in their entity. Alternatively, the HCO12 transgenic mice described in Example 1, subsection II, can be used to generate human anti-PA antibodies.

HuMAb Immunizations

To generate fully human monoclonal antibodies to protective antigen, HuMAb mice can be immunized with a purified or enriched preparation of anthrax PA83 or PA63 or both and/or cells expressing protective antigen, as described by Lonberg, N. et al. (1994) Nature 368(6474): 856-859; Fishwild, D. et al. (1996) Nature Biotechnology 14: 845-851 and WO 98/24884. Preferably, the mice will be 6-16 weeks of age upon the first infusion. For example, a purified preparation (5-20 μg) of protective antigen (kindly supplied by Stephen Little, U.S. Army Medical Research Institute of Infectious Disease) can be used to immunize the HuMAb mice intraperitoneally. Mice can also be immunized with transfected cells expressing protective antigen to promote immune responses.

Cumulative experience with various antigens has shown that the HuMAb transgenic mice respond best when initially immunized intraperitoneally (IP) with antigen in complete Freund's adjuvant, followed by every other week i.p. immunizations (up to a total of 6) with antigen in incomplete Freund's adjuvant. The immune response can be monitored over the course of the immunization protocol with plasma samples being obtained by retroorbital bleeds. The plasma can be screened by ELISA (as described below), and mice with sufficient titers of anti-PA human immunoglobulin can be used for fusions. Mice can be boosted intravenously with antigen 3 days before sacrifice and removal of the spleen. It is expected that 2-3 fusions for each antigen may need to be performed. Several mice will be immunized for each antigen. For example, a total of twelve HuMAb mice of the HC07 and HC012 strains can be immunized.

Generation of Hybridomas Producing Human Monoclonal Antibodies to Protective Antigen The mouse splenocytes can be isolated and fused with PEG to a mouse myeloma cell line based upon standard protocols. The resulting hybridomas are then screened for the production of antigen-specific antibodies. For example, single cell suspensions of splenic lymphocytes from immunized mice are fused to one-sixth the number of P3X63-Ag8.653 nonsecreting mouse myeloma cells (ATCC, CRL 1580) with 50% PEG. Cells are plated at approximately $2\times10^5$ in flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1× HAT (Sigma; the HAT is added 24 hours after the fusion). After two weeks, cells are cultured in medium in which the HAT is replaced with HT. Individual wells are then screened by ELISA for human anti-PA monoclonal IgM and IgG antibodies. Once extensive hybridoma growth occurs, medium is observed usually after 10-14 days. The antibody secreting hybridomas are replated, screened again, and if still positive for human IgG, anti-PA monoclonal antibodies, can be subcloned at least twice by limiting dilution. The stable subclones are then cultured in vitro to generate small amounts of antibody in tissue culture medium for characterization.

Generation of Transfectomas Producing Human Monoclonal Antibodies to Anthrax Protective Antigen Human antibodies of the invention can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or β-globin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13).

Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS0 myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, *Nature* 332:323-327; Jones, P. et al., 1986, *Nature* 321:522-525; and Queen, C. et al., 1989, *Proc. Natl. Acad. See. U.S.A.* 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999, which is herein incorporated by referenced for all purposes). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. For this reason, it is necessary to use the corresponding germline leader sequence for expression constructs. To add missing sequences, cloned cDNA sequences cab be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:19867-19870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assemble into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCV products. These overlapping products are then combined by PCT amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors for human IgGκ are described below. The plasmids were constructed so that PCR amplified V heavy and V kappa light chain cDNA sequences could be used to reconstruct complete heavy and light chain minigenes. These plasmids can be used to express completely human, or chimeric $IgG_1\kappa$ or $IgG_4\kappa$ antibodies. Similar plasmids can be constructed for expression of other heavy chain isotypes, or for expression of antibodies comprising lambda light chains.

Thus, in another aspect of the invention, the structural features of a human anti-PA antibody of the invention, e.g., 5E8, 2D5, 2H4, or 5D5, are used to create structurally related human anti-PA antibodies that retain at least one functional property of the antibodies of the invention, such as binding to protective antigen. More specifically, one or more CDRs of 5E8, 2D5, 2H4, or 5D5 can be combined recombinantly with known human framework regions and CDRs to create additional, recombinantly-engineered, human anti-PA antibodies of the invention.

Accordingly, in another embodiment, the invention provides a method for preparing an anti-PA antibody comprising:

preparing an antibody comprising (1) human heavy chain framework regions and human heavy chain CDRs, wherein at least one of the human heavy chain CDRs comprises an amino acid sequence selected from the amino acid sequences of CDRs shown in FIGS. 1, 4, 6 or 8 (SEQ ID NOs: 20, 22, 24, 38, 40, 42, 50, 52, 54, 62, 64, and 66); and (2) human light chain framework regions and human light chain CDRs, wherein at least one of the light chain CDRs comprises an amino acid sequence selected from the amino acid sequences of CDRs shown in FIGS. 2, 3, 5, 7, or 9 (SEQ ID NOs: 26, 28, 30, 32, 34, 36, 44, 46, 48, 56, 58, 60, 68, 70, and 72);

wherein the antibody retains the ability to bind to protective antigen. The ability of the antibody to bind protective antigen can be determined using standard binding assays, such as those set forth in the Examples (e.g., an ELISA).

Since it is well known in the art that antibody heavy and light chain CDR3 domains play a particularly important role in the binding specificity/affinity of an antibody for an antigen, the recombinant antibodies of the invention prepared, as set forth above, preferably comprise the heavy and light chain CDR3s of 5E8, 2D5, 2H4, or 5D5. The antibodies further can comprise the CDR2s of 5E8, 2D5, 2H4 or 5D5. The antibodies further can comprise the CDR1s of 5E8, 2D5, 2H4 or 5D5. An antibody of the invention can further comprise any combination of the CDRs.

Accordingly, in another embodiment, the invention further provides anti-PA antibodies comprising: (1) human heavy chain framework regions, a human heavy chain CDR1 region, a human heavy chain CDR2 region, and a human heavy chain CDR3 region, wherein the human heavy chain CDR3 region is the heavy chain CDR3 of 5E8, 2D5, 2H4 or 5D5 as shown in FIGS. 1, 4, 6 or 8 (SEQ ID NOs: 20, 38, 50, and 62); and (2) human light chain framework regions, a human light chain CDR1 region, a human light chain CDR2 region, and a human light chain CDR3 region, wherein the human light chain CDR3 region is the light chain CDR3 of 5E8, 2D5, 2H4 or 5D5 as shown in FIGS. 2, 3, 5, 7 or 9 (SEQ ID NO: 26, 32, 44, 56, and 68), wherein the antibody binds protective antigen. The antibody may further comprise the heavy chain CDR2 and/or the light chain CDR2 of 5E8, 2D5, 2H4 or 5D5. The antibody may further comprise the heavy chain CDR1 and/or the light chain CDR1 of 5E8, 2D5, 2H4 or 5D5.

The CDR1, CDR2, and/or CDR3 regions of an antibody of the invention, described above, can comprise the exact amino acid sequence(s) as those of 5E8, 2D5, 2H4 or 5D5 disclosed herein. However, one of ordinary skill in the art will appreciate that some deviation from the exact CDR sequences of 5E8, 2D5, 2H4 or 5D5 is possible while still retaining the ability of the antibody to bind protective antigen effectively. Accordingly, in another embodiment, the antibodies of the invention can contain of one or more CDRs that are, for example, 95%, 98% or 99.5% identical to one or more CDRs of 5E8, 2D5, 2H4 or 5D5.

Characterization of Binding of Human Monoclonal Antibodies to Protective Antigen To characterize binding of a human monoclonal anti-PA antibody of the invention, samples containing the antibody, e.g., sera from immunized mice, can be tested, e.g., by ELISA. In a typical (but non-limiting) example of an ELISA protocol, microtiter plates are coated with purified protective antigen at 20 μg/ml in PBS, and then blocked with 5% bovine serum albumin in PBS. Dilutions of plasma containing the anti-PA antibody are added to each well and incubated for 1-2 hours at 37° C. The plates are washed with PBS/Tween and then incubated with a goat-anti-human IgG Fc-specific polyclonal reagent conjugated to alkaline phosphatase for 1 hour at 37° C. After washing, the plates are developed with pNPP substrate (1 mg/ml), and analyzed at $OD_{405-650}$. Preferably, mice which develop the highest titers will be used for fusions.

An ELISA assay as described above can also be used to screen for hybridomas that show positive reactivity with PA immunogen. Hybridomas that bind with high avidity to protective antigen will be subcloned and further characterized. Clones from each hybridoma, which retain the reactivity of the parent cells (by ELISA), can be chosen for making a 5-10 vial cell bank stored at −140° C., and for antibody purification.

To purify human anti-PA antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected human anti-PA monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using protective antigen coated-ELISA plates as described above. Biotinylated MAb binding can be detected with a strep-avidin-alkaline phosphatase probe.

To determine the isotype of purified antibodies, isotype ELISAs can be performed. For example, wells of microtiter plates can be coated with 10 μg/ml of anti-human Ig overnight at 4° C. After blocking with 5% BSA, the plates are reacted with 10 μg/ml of monoclonal antibodies or purified isotype controls, at ambient temperature for two hours. The wells can then be reacted with either human IgG1 or human IgM-specific alkaline phosphatase-conjugated probes. Plates are developed and analyzed as described above.

Anti-PA human IgGs can be further tested for reactivity with protective antigen by Western blotting. For example, PA can be subjected to sodium dodecyl sulfate (SDS) polyacrylamide gel electrophoresis. After electrophoresis, the separated antigens will be transferred to nitrocellulose membranes, blocked with 20% mouse serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

II. Production of Transgenic Nonhuman Animals which Generate Human Monoclonal Anti-PA Antibodies In yet another aspect, the invention provides transgenic and transchromosomal nonhuman animals, such as transgenic or transchromosomal mice, which are capable of expressing human monoclonal antibodies that specifically bind to protective antigen. In a particular embodiment, the invention provides a transgenic or transchromosomal mouse having a genome comprising a human heavy chain transgene, such that the mouse produces human anti-PA antibodies when immunized with anthrax protective antigen and/or cells expressing protective antigen. The human heavy chain transgene can be integrated into the chromosomal DNA of the mouse, as is the case for transgenic, e.g., HuMAb Mouse®, as described in detail and exemplified herein. Alternatively, the human heavy chain transgene can be maintained extrachromosomally, as is the case for transchromosomal (e.g., KM-Mouse®) mice as described in WO 02/43478. Such transgenic and transchromosomal animals are capable of producing multiple isotypes of human monoclonal antibodies to protective antigen (e.g., IgG, IgA and/or IgE) by undergoing V-D-J recombination and isotype switching. Isotype switching may occur by, e.g., classical or non-classical isotype switching.

The design of a transgenic or transchromosomal nonhuman animal that responds to foreign antigen stimulation with a heterologous antibody repertoire, requires that the heterologous immunoglobulin transgenes contained within the transgenic animal function correctly throughout the pathway of B-cell development. This includes, for example, isotype switching of the heterologous heavy chain transgene. Accordingly, transgenes are constructed so as to produce isotype switching and one or more of the following of antibodies: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology,* 2nd edition (1989), Paul William E., ed. Raven Press, N.Y.

In certain embodiments, the transgenic or transchromosomal nonhuman animals which can be used to generate human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in the B-cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills et al., *Nucl. Acids Res.* 15:7305-7316 (1991); Sideras et al., *Intl. Immunol.* 1:631-642 (1989)). For each of the foregoing transgenic animals, functionally rearranged heterologous heavy and light chain immunoglobulin transgenes are found in a significant fraction of the B-cells of the transgenic animal (at least 10 percent).

The transgenes used to generate the transgenic nonhuman animals used to produce the human monoclonal antibodies of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic animal in that they are derived from, or correspond to, DNA encoding immunoglobulin heavy and light chain gene segments from a species not consisting of the transgenic nonhuman animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic animal when exposed to Protective antigen.

In an alternate embodiment, the transgenes comprise an unrearranged "mini-locus". Such transgenes typically comprise a substantial portion of the C, D, and J segments as well as a subset of the V gene segments. In such transgene constructs, the various regulatory sequences, e.g., promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the nonhuman animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

In a preferred embodiment of the invention, the transgenic or transchromosomal animal used to generate human antibodies to protective antigen contains at least one, typically 2-10, and sometimes 25-50 or more copies of the transgene described in Example 12 of WO 98/24884 (e.g., pHC1 or pHC2) bred with an animal containing a single copy of a light chain transgene described in Examples 5, 6, 8, or 14 of WO 98/24884, and the offspring bred with the $J_H$ deleted animal described in Example 10 of WO 98/24884. Animals are bred to homozygosity for each of these three traits. Such animals have the following genotype: a single copy (per haploid set of chromosomes) of a human heavy chain unrearranged minilocus (described in Example 12 of WO 98/24884), a single copy (per haploid set of chromosomes) of a rearranged human K light chain construct (described in Example 14 of WO 98/24884), and a deletion at each endogenous mouse heavy chain locus that removes all of the functional $J_H$ segments (described in Example 10 of WO 98/24884). Such animals are bred with mice that are homozygous for the deletion of the $J_H$ segments (Example 10 of WO 98/24884) to produce offspring that are homozygous for the $J_H$ deletion and hemizygous for the human heavy and light chain constructs. The resultant animals are injected with antigens and used for production of human monoclonal antibodies against these antigens.

B cells isolated from such an animal are monospecific with regard to the human heavy and light chains because they contain only a single copy of each gene. Furthermore, they will be monospecific with regards to human or mouse heavy chains because both endogenous mouse heavy chain gene copies are nonfunctional by virtue of the deletion spanning the $J_H$ region introduced as described in Examples 9 and 12 of WO 98/24884. Furthermore, a substantial fraction of the B cells will be monospecific with regards to the human or mouse light chains because expression of the single copy of the rearranged human κ light chain gene will allelically and isotypically exclude the rearrangement of the endogenous mouse κ and lambda chain genes in a significant fraction of B-cells.

Preferred transgenic and transchromosomal nonhuman animals, e.g., mice, will exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, preferably 0.5 to 5 mg/ml, ideally at least about 1.0 mg/ml. When a transgene capable of effecting a switch to IgG from IgM has been introduced into the transgenic mouse, the adult mouse ratio of serum IgG to IgM is preferably about 10:1. The IgG to IgM ratio will be much lower in the immature mouse. In general, greater than about 10%, preferably 40 to 80% of the spleen and lymph node B cells express exclusively human IgG protein.

The repertoire will ideally approximate that shown in a native mouse, usually at least about 10% as high, preferably 25 to 50% or more. Generally, at least about a thousand different immunoglobulins (ideally IgG), preferably $10^4$ to $10^6$ or more, will be produced, depending primarily on the number of different V, J and D regions introduced into the mouse genome. These immunoglobulins will typically recognize about one-half or more of highly antigenic proteins, e.g., *staphylococcus* protein A. Typically, the immunoglobulins will exhibit an affinity ($K_D$) for preselected antigens of below $10^{-7}$ M, such as of below $10^{-8}$ M, $10^{-9}$ M or $10^{-10}$ M, or even lower. In some embodiments, it may be preferable to generate nonhuman animals with predetermined repertoires to limit the selection of V genes represented in the antibody response to a predetermined antigen type. A heavy chain transgene having a predetermined repertoire may comprise, for example, human $V_H$ genes which are preferentially used in antibody responses to the predetermined antigen type in humans. Alternatively, some $V_H$ genes may be excluded from a defined repertoire for various reasons (e.g., have a low likelihood of encoding high affinity V regions for the predetermined antigen; have a low propensity to undergo somatic mutation and affinity sharpening; or are immunogenic to certain humans). Thus, prior to rearrangement of a transgene containing various heavy or light chain gene segments, such gene segments may be readily identified, e.g., by hybridization or DNA sequencing, as being from a species of organism other than the transgenic animal.

Transgenic and transchromosomal nonhuman animals, e.g., mice, as described above can be immunized with, for example, a purified or recombinant preparation of Protective antigen and/or cells expressing protective antigen. Alternatively, the transgenic animals can be immunized with DNA encoding human protective antigen. The animals will then produce B cells which undergo class-switching via intratransgene switch recombination (cis-switching) and express immunoglobulins reactive with protective antigen. The immunoglobulins can be human antibodies (also referred to as "human sequence antibodies"), wherein the heavy and light chain polypeptides are encoded by human transgene sequences, which may include sequences derived by somatic mutation and V region recombinatorial joints, as well as germline-encoded sequences; these human antibodies can be referred to as being substantially identical to a polypeptide sequence encoded by a human $V_L$ or $V_H$ gene segment and a human $J_L$ or $D_H$ and $J_H$ segment, even though other non-germline sequences may be present as a result of somatic mutation and differential V-J and V-D-J recombination joints. The variable regions of each antibody chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) which are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

Human antibodies which bind to the predetermined antigen can result from isotype switching, such that human antibodies comprising a human sequence γ chain (such as γ1, γ2a, γ2B, or γ3) and a human sequence light chain (such as kappa) are produced. Such isotype-switched human antibodies often contain one or more somatic mutation(s), typically in the variable region and often in or within about 10 residues of a CDR) as a result of affinity maturation and selection of B cells by antigen, particularly subsequent to secondary (or subsequent) antigen challenge. These high affinity human antibodies may have binding affinities ($K_D$) of below $10^{-7}$ M, such as of below $10^{-8}$ M, $10^{-9}$ M or $10^{-10}$ M, or even lower.

Another aspect of the invention includes B cells derived from transgenic or transchromosomal nonhuman animals as described herein. The B cells can be used to generate hybridomas expressing human monoclonal antibodies which bind with high affinity (e.g., lower than $10^{-7}$ M) to human protective antigen. Thus, in another embodiment, the invention provides a hybridoma which produces a human antibody having an affinity ($K_D$) of below $10^{-7}$ M, such as of below $10^{-8}$ M, $10^{-9}$ M or $10^{-10}$ M, or even lower when determined by surface plasmon resonance (SPR) technology in a BIACORE 3000 instrument using recombinant human protective antigen as the analyte and the antibody as the ligand for binding human protective antigen, wherein the antibody comprises:

a human sequence light chain composed of (1) a light chain variable region having a polypeptide sequence which is substantially identical to a polypeptide sequence encoded by a human $V_L$ gene segment and a human $J_L$ segment, and (2) a light chain constant region having a polypeptide sequence which is substantially identical to a polypeptide sequence encoded by a human $C_L$ gene segment; and a human sequence heavy chain composed of a (1) a heavy chain variable region having a polypeptide sequence which is substantially identical to a polypeptide sequence encoded by a human $V_H$ gene segment, optionally a D region, and a human $J_H$ segment, and (2) a constant region having a polypeptide sequence which is substantially identical to a polypeptide sequence encoded by a human $C_H$ gene segment.

The development of high affinity human monoclonal antibodies against protective antigen can be facilitated by a method for expanding the repertoire of human variable region gene segments in a transgenic nonhuman animal having a genome comprising an integrated human immunoglobulin transgene, said method comprising introducing into the genome a V gene transgene comprising V region gene segments which are not present in said integrated human immunoglobulin transgene. Often, the V region transgene is a yeast artificial chromosome comprising a portion of a human $V_H$ or $V_L$ ($V_K$) gene segment array, as may naturally occur in a human genome or as may be spliced together separately by recombinant methods, which may include out-of-order or omitted V gene segments. Often at least five or more functional V gene segments are contained on the YAC. In this variation, it is possible to make a transgenic animal produced by the V repertoire expansion method, wherein the animal expresses an immunoglobulin chain comprising a variable region sequence encoded by a V region gene segment present on the V region transgene and a C region encoded on the human Ig transgene. By means of the V repertoire expansion method, transgenic animals having at least 5 distinct V genes can be generated; as can animals containing at least about 24 V genes or more. Some V gene segments may be non-functional (e.g., pseudogenes and the like); these segments may be retained or may be selectively deleted by recombinant methods available to the skilled artisan, if desired.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a nonhuman animal germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous replication in yeast; such sequences may optionally be removed by genetic engineering (e.g., restriction digestion and pulsed-field gel electrophoresis or other suitable method) after replication in yeast is no longer necessary (i.e., prior to introduction into a mouse ES cell or mouse prozygote). Methods of propagating the trait of human sequence immunoglobulin expression, include breeding a transgenic animal having the human Ig transgene(s), and optionally also having a functional YAC having an expanded V segment repertoire. Both $V_H$ and $V_L$ gene segments may be present on the YAC. The transgenic animal may be bred into any background desired by the practitioner, including backgrounds harboring other human transgenes, including human Ig transgenes and/or transgenes encoding other human lymphocyte proteins. The invention also provides a high affinity human sequence immunoglobulin produced by a transgenic mouse having an expanded V region repertoire YAC transgene. Although the foregoing describes a preferred embodiment of the transgenic animal used to produce the human monoclonal antibodies of the invention, other embodiments are contemplated which have been classified in four categories:

I. Transgenic animals containing an unrearranged heavy and rearranged light immunoglobulin transgene;

II. Transgenic animals containing an unrearranged heavy and unrearranged light immunoglobulin transgene;

III. Transgenic animals containing a rearranged heavy and an unrearranged light immunoglobulin transgene; and IV. Transgenic animals containing a rearranged heavy and rearranged light immunoglobulin transgene.

Of these categories of transgenic animal, the order of preference is as follows II>I>III>IV where the endogenous light chain genes (or at least the K gene) have been knocked out by homologous recombination (or other method) and I>II>III>IV where the endogenous light chain genes have not been knocked out and must be dominated by allelic exclusion.

III. Bispecific/Multispecific Molecules which Bind to Protective Antigen

In yet another embodiment of the invention, human monoclonal antibodies to protective antigen, or antigen-binding portions thereof, can be derivatized or linked to another functional molecule, e.g., another peptide or protein (e.g., an Fab' fragment) to generate a bispecific or multispecific molecule which binds to multiple binding sites or target epitopes. For example, an antibody or antigen-binding portion of the invention can be functionally linked (e.g., by chemical coupling, genetic fusion, noncovalent association or otherwise) to one or more other binding molecules, such as another antibody, antibody fragment, peptide or binding mimetic.

Accordingly, the present invention includes bispecific and multispecific molecules comprising at least one first binding specificity for protective antigen and a second binding specificity for a second target epitope.

In one embodiment, the bispecific and multispecific molecules of the invention comprise as a binding specificity at least one antibody, or an antibody fragment thereof, including, e.g., an Fab, Fab', $F(ab')_2$, Fv, or a single chain Fv. The antibody may also be a light chain or heavy chain dimer, or any minimal fragment thereof such as a Fv or a single chain construct as described in Ladner et al. U.S. Pat. No. 4,946,778, issued Aug. 7, 1990, the contents of which is expressly incorporated by reference.

While human monoclonal antibodies are preferred, other antibodies which can be employed in the bispecific or multispecific molecules of the invention are murine, chimeric and humanized monoclonal antibodies.

Chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, Science 229:1202-1207 and by Oi et al., 1986, *BioTechniques* 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution U.S. Pat. No. 5,225,539; Jones et al. 1986 Nature 321:552-525; Verhoeyan et al. 1988 Science 239:1534; and Beidler et al. 1988 J. Immunol. 141:4053-4060.

All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A, filed Mar. 26, 1987), the content of which is expressly incorporated by reference. The human CDRs may be replaced with non-human CDRs using oligonucleotide site-directed mutagenesis as described in International Application WO 94/10332 entitled, *Humanized Antibodies to Fc Receptors for Immunoglobulin G on Human Mononuclear Phagocytes.*

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances. Antibodies in which amino acids have been added, deleted, or substituted are referred to herein as modified antibodies or altered antibodies.

The term modified antibody is also intended to include antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody. Any modification is within the scope of the invention so long as the bispecific and multispecific molecule has at least one antigen binding region specific for an FcγR and triggers at least one effector function.

Bispecific and multispecific molecules of the present invention can be made using chemical techniques (see e.g., D. M. Kranz et al. (1981) *Proc. Natl. Acad. Sci. USA* 78:5807), "polydoma" techniques (See U.S. Pat. No. 4,474,893, to Reading), or recombinant DNA techniques.

In particular, bispecific and multispecific molecules of the present invention can be prepared by conjugating the constituent binding specificities, e.g., the anti-FcR and anti-PA binding specificities, using methods known in the art and described in the examples provided herein. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described by Paulus (Behring Ins. Mitt. (1985) No. 78, 118-132); Brennan et al. (Science (1985) 229:81-83), and Glennie et al. (J. Immunol. (1987) 139: 2367-2375). Preferred conjugating agents are SATA and sulfo-SMCC, both available from Pierce Chemical Co. (Rockford, Ill.).

When the binding specificities are antibodies (e.g., two humanized antibodies), they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a MAb×MAb, MAb×Fab, Fab× F(ab')$_2$ or ligand×Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., toxin neutralization assay), or a Western blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

V. Pharmaceutical Compositions

In another aspect, the present invention provides a composition, e.g., a pharmaceutical composition, containing one or a combination of human anti-PA monoclonal antibodies, or antigen-binding portion(s) thereof, formulated together with a pharmaceutically acceptable carrier. Thus, in one embodiment, the compositions include a combination of multiple (e.g., two or more) isolated human anti-PA antibodies or antigen-binding portions thereof of the invention. Preferably, each of the antibodies or antigen-binding portions thereof of the composition binds to a distinct, pre-selected epitope of protective antigen.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifingal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above.

Any mode of parenteral administration is suitable for use in the present invention. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399, 163; 5,383,851; 5,312,335; 5,064,413; 4,941,880; 4,790,824; or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes.

For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) FEBS Lett. 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the desired area, e.g., the site of inflammation or infection. The composition must be fluid to the extent that easy syringability exists. It must be stable under the conditions of manufacture and storage and must be preserved against the contaminating action of microorganisms such as bacteria and fungi.

The term "therapeutically effective" in reference to dose of an antibody of the invention means an amount of the antibody which reduces a sign or a symptom associated with anthrax infection by at least about 20%, preferably by at least about 40%, more preferably by at least about 60%, even more preferably by at least about 80%, and most preferably by complete reduction relative to untreated subjects. Preferably, a therapeutically effective amount of an antibody of the invention is an amount sufficient to prevent death in a subject exposed to anthrax. The ability of an antibody of the invention to reduce signs and/or symptoms, including preventing death, associated with anthrax infection can be evaluated in an animal model system predictive of efficacy of the antibody in treating human anthrax infection. An example of such a model is described in Examples 6-8, infra, which provide a rabbit studies where animals were infected with anthrax and then treated with an antibody of the invention.

Alternatively, a therapeutically effective amount of an antibody of the invention can be evaluated by examining the antibody's ability to neutralize an anthrax toxin in vitro in a toxin neutralization assay, which is well known in the art and described supra. One of ordinary skill in the art would be able to determine such therapeutically effective amounts based on factors such as the subject's size, the severity of the signs and/or subject's symptoms, and the particular composition or route of administration selected.

Compositions containing an antibody of the invention for therapeutic use must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

VI. Uses and Methods of the Invention

The human antibodies, antibody compositions and methods of the present invention have numerous in vitro and in vivo diagnostic and therapeutic utilities involving the diagnosis, prevention and treatment of anthrax infection. For example, these antibodies can be administered to human subjects to treat and/or prevent anthrax infection. In addition, a blood or tissue sample can be removed from a subject and contacted with an antibody of the invention under conditions which allow detection of anthrax PA in the sample in order to diagnose an anthrax infection in the subject. As used herein, the term "subject" is intended to include human and non-human animals.

In a particular embodiment, the antibodies (e.g., human antibodies, multispecific and bispecific molecules and compositions) are used in vivo to treat, prevent or diagnose anthrax infection. In one prophylactic use, the subject has not been exposed to anthrax, and therefore can undergo a prophylactic-preexposure treatment with a human antibody of the invention to prevent infection by anthrax. In another prophylactic use, a subject known to have been exposed to anthrax, but who does not display signs or symptoms of disease, can undergo a post-exposure prophylactic treatment to prevent the pathology associated with anthrax disease progression. In a therapeutic treatment, the subject has been exposed to anthrax, is infected and exhibits signs and/or symptoms of the disease. Antibodies of the invention can be used in both of the prophylactic settings and in therapeutic treatment of anthrax.

For example, the human antibodies, antibody compositions and methods of the present invention can be used to treat a subject which has been (or suspected of having been) infected with *B. anthracis* and/or displays signs and/or symptoms of anthrax infection. Signs and/or symptoms of a subject infected with anthrax, or potentially infected, are measurable. For example, signs can include low $pO_2$ (oxygen in blood), elevated body temperature (measured fever), adventitious sounds on lung exam, low blood pressure (or other signs of shock), widened mediastinum on chest X ray (e.g., due to lysis of lymphnodes draining the lungs), or other signs typically known to be associated with uncontrolled pulmonary anthrax infection and toxin release; symptoms can include shortness of breath, cough, chills, feeling feverish, weakness, pain with deep breath, or other symptoms generally associated with pulmonary anthrax. Cutaneous anthrax begins as a pruritic papule or vesicle that enlarges and erodes (1-2 days) leaving a necrotic ulcer with subsequent formation of a central black eschar. Gastrointestinal anthrax may result in pharyngeal lesions with sore throat, dypshagia marked neck swelling and regional lymphadenopathy, or intestinal infection characterized by fever, severe abdominal pain, massive ascites, hematemesis, and bloody diarrhea. As with any form of anthrax, hemorrhagic meningitis can result from hematogenous spread of the organism from the primary site.

In one embodiment, the antibodies (e.g., human monoclonal antibodies, multispecific and bispecific molecules and compositions) of the invention can be used to detect levels of protective antigen in a biological sample (e.g., in blood from an anthrax-infected subject), which levels can then be linked to certain disease symptoms. This can be achieved using conventional detection assays known in the art, e.g., by contacting a sample and a control sample with the anti-PA antibody under conditions that allow for the formation of a complex between the antibody and protective antigen. Any complexes formed between the antibody and protective antigen are detected and compared between the sample and the control.

In another embodiment, the antibodies (e.g., human antibodies, multispecific and bispecific molecules and compositions) of the invention can be initially tested for binding activity associated with therapeutic or diagnostic use in vitro. For example, compositions of the invention can be tested using the ELISA and flow cytometric assays described in the Examples below.

The antibodies (e.g., human antibodies, multispecific and bispecific molecules and compositions) of the invention have additional utility in therapy and diagnosis of anthrax. For example, the human monoclonal antibodies, the multispecific or bispecific molecules can be used to elicit in vivo or in vitro one or more of the following biological activities: (1) prevent entry or translocation of anthrax toxin into the cell; (2) prevent binding of protective antigen to ATR on cells that express ATR; (3) inhibit cleavage of PA83 to PA63; (4) prevent formation of the PA heptamer; (5) block or reduce binding of a toxin (edema factor or lethal factor) to the heptamer; (6) neutralize lethal factor or edema factor such that the toxins are unable to cause physiological damage to the cell; and/or (7) otherwise protect cells against the lethal effects of toxins.

Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous) as described supra. Suitable dosages of the molecules used will depend on the age and weight of the subject and the concentration and/or formulation of the antibody composition. A therapeutically effective dosage of antibody of the present invention for administration to a patient in need of (i) treatment (i.e., infection with anthrax and showing clinical signs and/or symptoms), (ii) prophylactic treatment (e.g., prevention of clinical manifestations of anthrax such as neutropenia, clinical signs and/or clinical symptoms in patients suspected of exposure to anthrax or in patients infected with anthrax, but not showing clinical signs or symptoms), or (iii) prophylaxis (e.g., prevention of disease prior to exposure or infection by anthrax, including use in individuals who are allergic to antibiotics or where the anthrax is antibiotic resistant or in combination with vaccine therapy where the vaccine could take up to 18 months for efficacy), against anthrax infection includes dosages from 0.1 mg/kg to 100 mg/kg. In particular embodiments, the skilled practitioner may administer from 0.3 mg/kg to 50 mg/kg or from about 1 mg/kg to 12 mg/kg. The dosage will depend on, inter alia, the health of the patient, whether infection by anthrax is present, whether signs or symptoms of anthrax disease are present, and whether administration is for prophylaxis. The skilled practioner will appreciate that dosaging of an antibody of the invention can be modified depending on these factors.

The following dosaging regimens should, therefore, not be construed as limiting. For example, if a patient is diagnosed with anthrax infection and exhibits signs of anthrax infection then substantially high dose can be administered, e.g., at least 25 mg/kg, or 50 mg/kg or even 100 mg/kg, in order to save the patients life. Alternatively, a patient who is believed to be infected but exhibits no signs or symptoms can benefit from relatively lower dosage, e.g, less than 12-15 mg/kg or even 1-3 mg/kg. In the patient who receives an anthrax vaccine, and therefore it is desirable to provide a therapeutic antibody to provide immediate protection against any anthrax infection prior to suitable plasma levels of the patient's own antibodies from the vaccine, the practioner can use intermediate dosage ranges, e.g., 12-50 mg/kg.

Human anti-PA antibodies of the invention can be co-administered with one or more other therapeutic or immunostimulatory agents. The antibody can be administered before, after or concurrently with the agent or can be co-administered with other known therapies including Anthrax vaccines, antibodies against LF, EF, PA, and B. anthracis antibiotics, e.g., ciprofloxacin, doxycycline, chloramphenicol, clindamycin, tetracycline, rifampin, and vancomycin.

In a particular embodiment, the invention provides methods for detecting the presence of protective antigen in a sample, or measuring the amount of anthrax protective antigen, comprising contacting the sample, and a control sample, with a human monoclonal antibody of the invention, or an antigen binding portion thereof, which specifically binds to protective antigen, under conditions that allow for formation of a complex between the antibody or portion thereof and protective antigen. The formation of a complex is then detected, wherein a difference between complex formation of the sample compared to the control sample is indicative the presence of protective antigen in the sample.

Also within the scope of the present invention are kits comprising the antibody compositions of the invention (e.g., human antibodies and immunoconjugates) and instructions for use. The kit can further contain one or more additional diagnostic, therapeutic or immunostimulatory agents as described above. The present invention is further illustrated by the following examples which should not be construed as further limiting.

The invention also provides methods of screening to identify new antibodies having properties that make them useful in methods of treatment. Antibodies which are particularly useful in methods of treatment, in addition to having the neutralization activity as described supra, and in the Examples infra, include antibodies having one or more of the following characteristics: binds to Fc receptor for neutralization activity (e.g., as measured by use of Fc receptor blocking antibodies such as 2.4G2 or use of Fab'$_2$ or ScFv in TNA with at least 5-fold, more preferably 10-fold, reduction in activity); exhibits higher affinity for PA 63 over PA 83 (e.g., as measured by standard ELISA using 1 μg/ml antibody), does not bind PA 83 at 1 μg/ml, $OD_{405\ nm}$ 0.2 or less according to standard ELISA, does not block anthrax lethal factor/edema factor according to competition binding assay described in Little et al., 1996, Microbiology 142:707-715, or does not compete with an anti-PA antibody selected from murine 1G3, murine 2D5 and murine 14B7 in binding to PA 63 (e.g., as measured by standard ELISA competition assay). Antibodies having many or all of these characteristics are desirable for in vivo use. Particularly useful antibodies do not compete with an anti-PA antibody selected from murine 14B7 in binding to PA 63 (see Little et al., 1996, Microbiology 142:707-715), i.e., antibodies which block PA binding to ATR, and are desirable for in vivo therapy.

In a particular screening method of the invention, antibodies are selected based on (1) first selecting one or more antibodies which neutralizes anthrax toxin in a toxin neutralization assay, and (2) then selecting an antibody which has an $ED_{50}$ of 0.1 μg/ml or less in a TNA. In this method, an antigen-antibody binding affinity assay (e.g., ELISA) is not used prior to the TNA steps. This is in contrast with methods conventionally used in the prior art, which rely on antigen-antibody binding affinity assays as a first and primary method of screening. By including such a step many antibodies, which would otherwise demonstrate excellent toxin neutralizing activity, such as HuMAb 5E8, are excluded from further development. The present inventors have discovered that binding affinity to PA is not a useful criteria, and therefore it is omitted from selection methods of the present invention. Additional, selection steps can be practiced in addition to the two steps described above to obtain antibodies having the properties described.

EXAMPLES

Example 1

Preparation of Transgenic Animals which Express Fully Human Antibodies

I. Generation of Transgenic (Cmu Targeted) Mice

Construction of a CMD Targeting Vector

The plasmid pICEmu contains an EcoRI/XhoI fragment of the murine Ig heavy chain locus, spanning the mu gene, that was obtained from a Balb/C genomic lambda phage library (Marcu et al. Cell 22: 187, 1980). This genomic fragment was subcloned into the XhoI/EcoRI sites of the plasmid pICEMI9H (Marsh et al; Gene 32, 481-485, 1984). The heavy chain sequences included in pICEmu extend downstream of the EcoRI site located just 3' of the mu intronic enhancer, to the XhoI site located approximately 1 kb downstream of the last transmembrane exon of the mu gene; however, much of the mu switch repeat region has been deleted by passage in *E. coli.*

The targeting vector was constructed as follows. A 1.3 kb HindIII/SmaI fragment was excised from pICEmu and subcloned into HindIII/SmaI digested pBluescript (Stratagene, La Jolla, Calif.). This pICEmu fragment extends from the HindIII site located approximately 1 kb 5' of Cmu1 to the SmaI site located within Cmu1. The resulting plasmid was digested with SmaI/SpeI and the approximately 4 kb SmaI/XbaI fragment from pICEmu, extending from the SmaI site in Cmu1 3' to the XbaI site located just downstream of the last Cmu exon, was inserted. The resulting plasmid, pTAR1, was linearized at the SmaI site, and a neo expression cassette inserted. This cassette consists of the neo gene under the transcriptional control of the mouse phosphoglycerate kinase (pgk) promoter (XbaI/TaqI fragment; Adra et al. (1987) Gene 60: 65-74) and containing the pgk polyadenylation site (PvuII/HindIII fragment; Boer et al. (1990) Biochemical Genetics 28: 299-308). This cassette was obtained from the plasmid pKJ1 (described by Tybulewicz et al. (1991) Cell 65: 1153-1163) from which the neo cassette was excised as an EcoRI/HindIII fragment and subcloned into EcoRI/HindIII digested pGEM-7Zf (+) to generate pGEM-7 (KJ1). The neo cassette was excised from pGEM-7 (KJ1) by EcoRI/SalI digestion, blunt ended and subcloned into the SmaI site of the plasmid pTAR1, in the opposite orientation of the genomic Cmu sequences. The resulting plasmid was linearized with Not I, and a herpes simplex virus thymidine kinase (tk) cassette was inserted to allow for enrichment of ES clones bearing homologous recombinants, as described by Mansour et al. (1988) Nature 336: 348-352. This cassette consists of the coding sequences of the tk gene bracketed by the mouse pgk promoter and polyadenylation site, as described by Tybulewicz et al. (1991) Cell 65: 1153-1163. The resulting CMD targeting vector contains a total of approximately 5.3 kb of homology to the heavy chain locus and is designed to generate a mutant mu gene into which has been inserted a neo expression cassette in the unique SmaI site of the first Cmu exon. The targeting vector was linearized with PvuI, which cuts within plasmid sequences, prior to electroporation into ES cells.

Generation and Analysis of Targeted ES Cells

AB-1 ES cells (McMahon, A. P. and Bradley, A., (1990) Cell 62: 1073-1085) were grown on mitotically inactive SNL76/7 cell feeder layers (ibid.) essentially as described (Robertson, E. J. (1987) in *Teratocarcinomas and Embryonic Stem Cells: a Practical Approach* (E. J. Robertson, ed.) Oxford: IRL Press, p. 71-112). The linearized CMD targeting vector was electroporated into AB-1 cells by the methods described Hasty et al. (Hasty, P. R. et al. (1991) Nature 350: 243-246). Electroporated cells were plated into 100 mm dishes at a density of 1-2×$10^6$ cells/dish. After 24 hours, G418 (200 micrograms/ml of active component) and FIAU (5×$10^{-7}$ M) were added to the medium, and drug-resistant clones were allowed to develop over 8-9 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described Laird et al. (Laird, P. W. et al., (1991) Nucleic Acids Res. 19: 4293). Isolated genomic DNA was digested with SpeI and probed with a 915 bp SacI fragment, probe A (see FIG. 1), which hybridizes to a sequence between the mu intronic enhancer and the mu switch region. Probe A detects a 9.9 kb SpeI fragment from the wild type locus, and a diagnostic 7.6 kb band from a mu locus which has homologously recombined with the CMD targeting vector (the neo expression cassette contains a SpeI site). Of 1132 G418 and FIAU resistant clones screened by Southern blot analysis, 3 displayed the 7.6 kb SpeI band indicative of homologous recombination at the mu locus. These 3 clones were further digested with the enzymes BglI, BstXI, and EcoRI to verify that the vector integrated homologously into the mu gene. When hybridized with probe A, Southern blots of wild type DNA digested with BglI, BstXI, or EcoRI produce fragments of 15.7, 7.3, and 12.5 kb, respectively, whereas the presence of a targeted mu allele is indicated by fragments of 7.7, 6.6, and 14.3 kb, respectively. All 3 positive clones detected by the SpeI digest showed the expected BglI, BstXI, and EcoRI restriction fragments diagnostic of insertion of the neo cassette into the Cmu1 exon.

Generation of Mice Bearing the Mutated mu Gene

The three targeted ES clones, designated number 264, 272, and 408, were thawed and injected into C57BL/6J blastocysts as described by Bradley (Bradley, A. (1987) in *Teratocarcinomas and Embryonic Stem Cells: a Practical Approach*. (E. J. Robertson, ed.) Oxford: IRL Press, p. 113-151). Injected blastocysts were transferred into the uteri of pseudopregnant females to generate chimeric mice representing a mixture of cells derived from the input ES cells and the host blastocyst. The extent of ES cell contribution to the chimera can be visually estimated by the amount of agouti coat coloration, derived from the ES cell line, on the black C57BL/6J background. Clones 272 and 408 produced only low percentage chimeras (i.e. low percentage of agouti pigmentation) but clone 264 produced high percentage male chimeras. These chimeras were bred with C57BL/6J females and agouti offspring were generated, indicative of germline transmission of the ES cell genome. Screening for the targeted mu gene was carried out by Southern blot analysis of BglI digested DNA from tail biopsies (as described above for analysis of ES cell DNA). Approximately 50% of the agouti offspring showed a hybridizing BglI band of 7.7 kb in addition to the wild type band of 15.7 kb, demonstrating a germline transmission of the targeted mu gene.

Analysis of Transgenic Mice for Functional Inactivation of mu Gene

To determine whether the insertion of the neo cassette into Cmu1 has inactivated the Ig heavy chain gene, a clone 264 chimera was bred with a mouse homozygous for the JHD mutation, which inactivates heavy chain expression as a result of deletion of the JH gene segments (Chen et al, (1993) Immunol. 5: 647-656). Four agouti offspring were generated. Serum was obtained from these animals at the age of 1 month and assayed by ELISA for the presence of murine IgM. Two of the four offspring were completely lacking IgM (see Table 1). Genotyping of the four animals by Southern blot analysis of DNA from tail biopsies by BglI digestion and hybridization with probe A (see FIG. 1), and by StuI digestion and hybridization with a 475 bp EcoRI/StuI fragment (ibid.) demonstrated that the animals which fail to express serum IgM are those in which one allele of the heavy chain locus carries the JHD mutation, the other allele the Cmu1 mutation. Mice heterozygous for the JHD mutation display wild type levels of serum Ig. These data demonstrate that the Cmu1 mutation inactivates expression of the mu gene.

TABLE 1

| Mouse | Serum IgM (µg/ml) | Ig H chain genotype |
| --- | --- | --- |
| 42 | <0.002 | CMD/JHD |
| 43 | 196 | +/JHD |
| 44 | <0.002 | CMD/JHD |
| 45 | 174 | +/JHD |
| 129 × BL6 F1 | 153 | +/+ |
| JHD | <0.002 | JHD/JHD |

Table 1 shows the levels of serum IgM, detected by ELISA, for mice carrying both the CMD and JHD mutations (CMD/JHD), for mice heterozygous for the JHD mutation (+/JHD), for wild type (129Sv×C57BL/6J)F1 mice (+/+), and for B cell deficient mice homozygous for the JHD mutation (JHD/JHD).

II. Generation of HCO12 Transgenic Mice

The HCO12 human heavy transgene was generated by coinjection of the 80 kb insert of pHC2 (Taylor et al., 1994, Int. Immunol., 6: 579-591) and the 25 kb insert of pVx6. The plasmid pVx6 was constructed as described below.

An 8.5 kb HindIII/SalI DNA fragment, comprising the germline human $V_{H1}$-18 (DP-14) gene together with approximately 2.5 kb of 5' flanking, and 5 kb of 3' flanking genomic sequence was subcloned into the plasmid vector pSP72 (Promega, Madison, Wis.) to generate the plasmid p343.7.16. A 7 kb BamHI/HindIII DNA fragment, comprising the germline human $V_{H5}$-51 (DP-73) gene together with approximately 5 kb of 5' flanking and 1 kb of 3' flanking genomic sequence, was cloned into the pBR322 based plasmid cloning vector pGP1f (Taylor et al. 1992, Nucleic Acids Res. 20: 6287-6295), to generate the plasmid p251f. A new cloning vector derived from pGP1f pGP1k, was digested with EcoRV/BamHI, and ligated to a 10 kb EcoRV/BamHI DNA fragment, comprising the germline human $V_{H3}$-23 (DP47) gene together with approximately 4 kb of 5' flanking and 5 kb of 3' flanking genomic sequence. The resulting plasmid, p112.2RR.7, was digested with BamHI/SalI and ligated with the 7 kb purified BamHI/SalI insert of p251f. The resulting plasmid, pVx4, was digested with XhoI and ligated with the 8.5 kb XhoI/SalI insert of p343.7.16.

A clone was obtained with the $V_{H1}$-18 gene in the same orientation as the other two V genes. This clone, designated pVx6, was then digested with NotI and the purified 26 kb insert coinjected with the purified 80 kb NotI insert of pHC2 at a 1:1 molar ratio into the pronuclei of one-half day (C57BL/6J×DBA/2J)F2 embryos as described by Hogan et al. (B. Hogan et al., Manipulating the Mouse Embryo, A Laboratory Manual, $2^{nd}$ edition, 1994, Cold Spring Harbor Laboratory Press, Plainview N.Y.). Three independent lines of transgenic mice comprising sequences from both Vx6 and HC2 were established from mice that developed from the injected embryos. These lines are designated (HCO12) 14881, (HCO12) 15083, and (HCO12) 15087. Each of the three lines were then bred with mice comprising the CMD mutation described in Example 1, the JKD mutation (Chen et al. 1993, EMBO J. 12: 811-820), and the (KCo5) 9272 transgene (Fishwild et al. 1996, Nature Biotechnology 14: 845-851). The resulting mice express human immunoglobulin heavy and kappa light chain transgenes in a background homozygous for disruption of the endogenous mouse heavy and kappa light chain loci.

Example 2

Production of Fully Human Antibodies Against Anthrax Protective Antigen

Human monoclonal antibodies against anthrax protective antigen were produced as described below in transgenic mice generated as described supra.

Generation of Human Anti-PA Monoclonal Antibodies

Transgenic HuMAb Mouse®, strain HC2/KCo7, having four distinct genetic modifications was used for immunizations. These transgenic mice contain a human immunoglobulin gene miniloci that encodes unrearranged human heavy (µ and γ) and κ light chain immunoglobulin sequences, together with targeted mutations that inactivate the endogenous µ and κ chain loci. Accordingly, the mice exhibit no expression of mouse IgM or κ, and in response to immunization, the introduced human heavy and light chain transgenes undergo class switching and somatic mutation to generate high affinity human IgGκ monoclonal antibodies.

Mice were housed in filter cages and were evaluated to be in good physical condition on the dates of immunization, bleeds, and the day of the fusion. Fifteen micrograms of recombinant full-length anthrax PA83 in 150 µL PBS was mixed in complete Freund's adjuvant (Sigma F5881) or MPL+TDM (RIBI) adjuvant (Sigma M6536) 1:1 using an emulsifying needle. Mice were injected i.p. with 0.3 cc prepared antigen, and subsequently boosted 2 to 4 more times at 14 day intervals using the full-length PA83 incomplete Freunds (Sigma F5506) or RIBI (Sigma M6536), except HuMab 5E8 which was prepared by subsequently boosting with PA63. Antibody responses in the mice were monitored by ELISA using PA. Animals that developed anti-PA titers against the protective antigen, were given an i.v. injection of recombinant protective antigen seventy-two hours prior to fusion. The titers from individual mice varied between 1:200 and greater than 1:100,000. Mouse splenocytes were harvested, purified and fused.

Single-cell suspensions of splenic lymphocytes from immunized animals were fused with the murine myelanoma cell line P3X63Ag8.653 (American Type Culture Collection, Rockville Md.; ATCC CRL 1580, lot F-15183) in the presence of polyethylene glycol. The original ATCC vial was thawed and expanded in culture. A seed stock of frozen vials was prepared from this expansion. Cells were maintained in culture for 3-6 months, passed twice a week. P388D1 (ATCC TIB-63 FL) was expanded to 200 mL and exhausted. The supernatant was spun down and filtered and used as a media addition known as conditioned media. This cell line was passed for 3 to 6 months and then a new vial was thawed.

High Glucose DMEM (Mediatech, Cellgro #10013245) containing 5% FBS, and Penicillin-Strepatientomycin (Cellgro #30004030) was used to culture the myeloma and P388D1 cells. High Glucose DMEM (Mediatech, Cellgro #10013245) containing 5% FBS, and Penicillin-Strepatientomycin (Cellgro #30004030) was used to culture the myeloma and P388D1 cells. Additional media supplements were added to the Hybridoma growth media, which included: 3% Origen-Hybridoma Cloning Factor (Igen, 36335), 10% P388D1 conditioned media (Aug. 10, 1999 DH), 10% FBS (Hyclone, SH30071 lot #AGH6843), L-glutamine (Gibco #1016483) 0.1% gentamycin (Gibco #1020070), 2-mercapatienthanol (Gibco #1019091) HAT (Sigma, H0262) $1.0 \times 10^4$ M Hypoxanthine, $4.0 \times 10^{-7}$ M Aminopatienterin, $1.6 \times 10^{-5}$ M Thymidine).

Hybridomas were selected by the addition of HAT 24 hours after fusion. Hybridomas were first screened by a sandwich ELISA for human IgG producers. Briefly, hybridoma supernatants were captured with goat anti-human kappa (Southern Biotech, Birmingham Ala.), and then reacted with alkaline phophatase-conjugated goat anti-human IgG (gamma-chain specific) (Jackson ImmunoResearch Laboratories, Inc., West Grove, Pa.).

Figure 13:
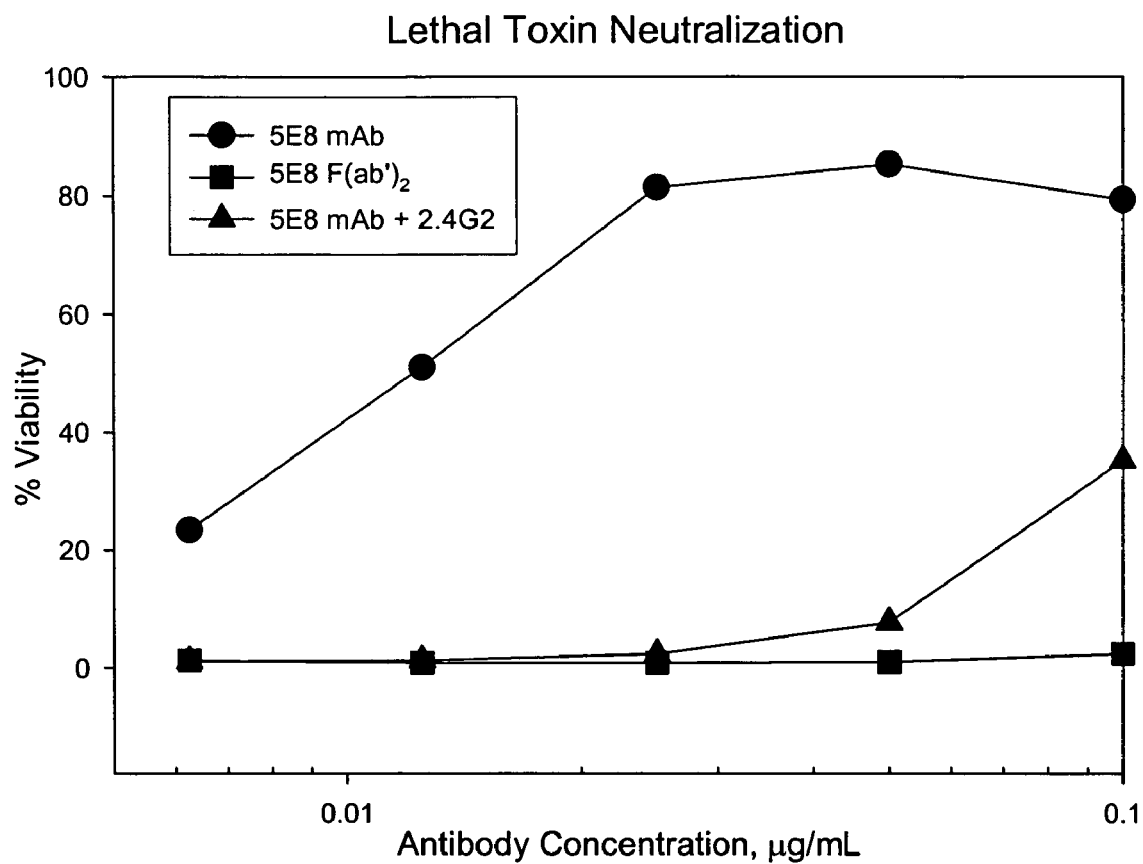
FIG. 13 is a graph showing comparison of neutralization of *B. anthracis* lethal toxin using the F(ab')$_2$ fragment of HuMAb 5E8 antibody and the intact 5E8 mAb in the absence or presence of anti-mouse FcRII/III monoclonal antibody 2.4G2.

Hybridomas producing specific human IgG-producing hybridomas were then screened using an in vitro toxin neutralization assay (Little et al., 1990, Infection and Immunity 65:5171-5175; see Example 3). Initially, the mAbs were tested for binding to anthrax protective antigen by ELISA using full length PA83. However, several mAbs that demonstrated good toxin neutralization activity (TNA) bound poorly by ELISA. Most of these antibodies reacted well with the cleaved PA63. As a result of this finding, the TNA was used as an initial screen followed by further characterization using ELISA. This protocol led to the isolation of at least four antibodies of interest, e.g., 5E8, 2D5, 2H4 and 5D5. The $V_H$ and $V_L$ regions of selected anti-PA HuMabs were then isolated from RNA from hybridomas, reverse transcribed to cDNA, and V regions amplified by PCR. The PCR product was sequenced as shown in Example 4.

HuMabs were then purified by protein A column chromatography using the following procedure: (1) Loading conditions: Supernatant was loaded on a 5 ml Protein-A column that was equilibrated with Phosphate buffered Saline (PBS); (2) Wash: PBS buffer; (3) Elution: 0.1 M Glycine with 150 mM NaCl, pH 2.9. The elute was neutralized with 1M Tris buffer (30 ul for every 2 ml fraction). Each eluted fraction was run on gel before being pooled. Once the purity by coomassie staining was verified, fractions were pooled and dialyzed against 10 mM sodium phosphate buffer with 150 mM $NaCl_2$, pH 7.2.

Example 3A

In Vitro Neutralization of Lethal Toxin by Anti-PA Human Monoclonal Antibodies TNA experiments were performed according to Little et al, 1990, supra. Briefly, the toxin-sensitive murine macrophage cell line J774A. 1 was exposed to a mixture of PA and LF (10:1) in the presence or absence of varying concentrations of anti-PA mAbs. After a 3 hour incubation, survival of the macrophages was determined using a viability dye (MTT). The results (FIG. 10) demonstrate the activity of the human anti-PA antibodies to neutralize lethal toxin in vitro. The following Table 2 indicates the effective dose of antibody required to maintain 50% viability ($ED_{50}$) of macrophages in the TNA.

TABLE 2

| Antibody | $ED_{50}$ (μg/mL) |
|---|---|
| 5D5 | 0.035 |
| 2H4 | 0.060 |
| 5E8 | 0.015 |
| 2D5 | 5 |

To test for direct binding to anthrax protective antigen, ELISA plates were coated with PA83 or PA63. The mAb samples were added at appropriate dilutions, and bound antibody was detected with anti-human IgG alkaline phophatase-conjugated probes. The plate was developed with a p-NPP substrate and the $OD_{405}$ determined on a Softmax plate reader. Binding rate constants were determined using plasmon resonance technology on a BIAcore instrument.

Preliminary binding data revealed that the dissociation constants for the HuMabs are in the nanomolar range. The binding activity results (FIG. 11) demonstrate that the human antibodies generated against rPA-83 bind to both the full length (83 kD) and cleaved (63 kD) forms of protective antigen. HuMabs 5D5, 2H4 and 5E8 exhibited greater reactivity to PA63 than PA83, possibly because after cleavage of the antigen more binding epitopes are exposed.

To determine the activity requirement for antibody neutralization of anthrax toxin, an additional toxin neutralization assay was performed as described using HuMAb 5E8 and murine 14B7, except that the antibodies were added either before addition of toxin (−30 min), at the same time as the addition of toxin (0 min.), 15 minutes after addition of toxin (+15 min.) or 30 minutes after the addition of the toxin (+30 min) (See FIG. 12).

The data show that HuMab 5E8 protects cells from anthrax toxin after exposure of cells to the toxin. In contrast to a murine antibody, which prevents PA83 binding to the receptor (murine mAb 14B7 used at 10× higher doses), HuMAb 5E8 continued to prevent cell death from anthrax toxin, even when added 15 minutes post addition of the PA83 and LF. These data indicate that HuMAb 5E8, which preferentially binds to cell-associated PA63 may be effective at rescuing cells from anthrax toxin death even after exposure. Therefore, HuMAb 5E8 and those with similar properties would be expected to have greater therapeutic activity, than antibodies that block receptor binding.

Example 3B

In Vitro Neutralization by Humab 5E8 Requires Fc Receptor Binding

A toxin neutralization assay was performed as previously described, except using the $F(ab')_2$ fragment of the 5E8 antibody and the intact 5E8 mAb in the absence or presence of anti-mouse FcRII/III monoclonal antibody 2.4G2, which specifically blocks Fc receptor and antibody Fc interactions (BD Biosciences Pharmingen, San Diego, Calif.). The $F(ab')_2$ fragment was prepared by pepsin digestion of the mAb 5E8 followed by purification of the $F(ab')_2$ using Protein A and Protein L column chromatography.

The results show that HuMab 5E8 requires Fc receptor binding for activity (see FIG. 13). The F(ab')₂ fragment of HuMAb 5E8, which retains full binding activity to PA 63, but does not have the capacity to engage Fc receptors, is not able to prevent death of macrophage-like cells. Additionally, 2.4G2 antibody, which specifically blocks Fc receptor and antibody Fc interactions, greatly reduced the anti-toxin activity of huMab 5E8.

Example 4

Antibody Sequencing

The $V_H$ and $V_L$ regions of four HuMabs were isolated from hybridoma RNA, reverse transcribed to cDNA, amplified by PCR and sequenced. The nucleic and amino acid sequences of the $V_H$ and $V_L$ regions of these HuMabs are provided below and in FIGS. 1-9. It is noted that the 5E8 hybridoma produces antibodies having a heavy chain that pairs with one of two light chains ($V_{L\ major}$ or $V_{L\ minor}$). Both antibodies (i.e., 5E8 $V_H/V_{L\ major}$ and 5E8' $V_H/V_L$ minor) bind to anthrax PA and can neutralize anthrax toxin according to the TNA.

The human germline sequences which produce the heavy chains of these antibodies include $V_{H3-33}$ and $V_{H3-7}$, while human germline sequence which produce the light chains include A27, L18, and L15, as noted in FIGS. 1-9. These germline sequences are well known in the art, and can be found in immunology reference texts and free internet web sites readily accessible, e.g., see Kabat et al., (1991) Sequences of Proteins of Immunological Interest. 5th edition. U.S. Dept of Health and Human Services, Public Health Service, NIH. NIH publication No. 91-3242 (updates available at immuno.bme.nwu.edu and ncbi.nlm.nih gov/repository/kabat) and www.mrc-cpe.cam.ac.uk/vbase-ok.php-?menu=901.

5E8 $V_H$ Nucleic Acid Sequence (SEQ ID NO:1)
caggtgcagctggtggagtctgggggaggcgtggtccagcctgggaggtc
cctgagactctcctgtgcagcgtctggattcaccttcagttactatggca
tgcactgggtccgccaggctccaggcaaggggctggagtgggtggcagtt
atatggcatgatgaaagtattgtatactatgcagactccgtgaagggccg
attcaccatctccagagacaattccaagaacacgctgtatctgcaaatga
acagtctgagagccgaggacacggctgtgtattactgtacgagagaccct
ggggatccctattactactactacggtttggacgtctggggccaagggac
cacggtcaccgtctcctca 5E8 $V_H$ Amino Acid Sequence (SEQ ID NO:2)
QVQLVESGGGVVQPGRSLRLSCAASGFTFSYYGMHWVRQAPGKGLEWVAV
IWHDESIVYYADSVKGRFTISRDNSKNTLYLQMNSLRAEDTAVYYCTRDP
GDPYYYYYGLDVWGQGTTVTVSS 5E8 $V_L$ (Major) Nucleic Acid Sequence (SEQ ID NO: 3)
gaaattgtgttgacgcagtctccaggcaccctgtctttgtctccagggga
aagagccaccctctcctgcagggccagtcagagtgttagcagcagctact
tagcctggtaccagcagaaacctggccaggctcccaggctcctcatctat
ggtgcatccagcagggccactggcatcccagacaggttcagtggcagtgg
gtctgggacagacttcactctcaccatcagcagactggagcctgaagatt
ttgcagtgtattactgtcagcagtatggtagctcaatgtacacttttggc
caggggaccaagctagagatcaaa 5E8 $V_L$ (Major) Amino Acid Sequence (SEQ ID NO:4)
EIVLTQSPGTLSLSPGERATLSCRASQSVSSSYLAWYQQKPGQAPRLLIY
GASSRATGIPDRFSGSGSGTDFTLTISRLEPEDFAVYYCQQYGSSMYTFG
QGTKLEK 5E8' $V_L$ (Minor) Nucleic Acid Sequence (SEQ ID NO :5)
gaaattgtgttgacgcagtctccaggcaccctgtctttgtctccagggga
aagagccaccctctcctgcagggccagtcagagtgttagcagcagctact
tagcctggtaccagcagaaacctggccaggctcccaggctcctcatctat
ggtgcatccagcagggccactggcatcccagacaggttcagtggcagtgg
gtctgggacagacttcactctcaccatcagcagactggagcctgaagatt
ttgcagtgtattactgtcagcagtatggtagctcacctcccactttcggc
ggagggaccaaggtggagatcaaa 5E8' $V_L$ (Minor) Amino Acid Sequence (SEQ D NO:6)
EIVLTQSPGTLSLSPGERATLSCRASQSVSSSYLAWYQQKPGQAPRLLIY
GASSRATGIPDRFSGSGSGTDFTLTISRLEPEDFAVYYCQQYGSSPPTFG
GGTKVEIK 2D5 $V_H$ Nucleic Acid Sequence (SEQ ID NO:7)
caggtgcagctggtggagtctgggggaggcgtggtccagcctgggaggtc
cctgagactctcctgtgcagcgtctggattcaccttcagtagctatggca
tgcactgggtccgccaggctccaggcaaggggctggagtgggtggcagtt
atatggaatgatggaagtaataaatactatgcagactccgtgaagggccg
attcaccatctccagagacaattccaagaacacgctgtatctgcaaatga
acagcctgagagccgaggacacggctgtgtattactgtgcgagagaaaac
tggggagagtactttgactactggggccagggaaccctggtcaccgtctc
ctca

2D5 V<sub>H</sub> Amino Acid Sequence (SEQ ID NO:8)
QVQLVESGGGVVQPGRSLRLSCAASGFTFSSYGMHWVRQAPGKGLEWVAV
IWNDGSNKYYADSVKGRFTISRDNSKNTLYLQMNSLRAEDTAVYYCAREN
WGEYFDYWGQGTLVTVSS

2D5 V<sub>L</sub> Nucleic Acid Sequence (SEQ ID NO:9)
gccatccagttgacccagtctccatcctcctgtctgcatctgtaggaga
cagagtcaccatcacttgccgggcaagtcagggcattagcagtgctttag
cctggtatcagcagaaaccagggaaagctcctaagctcctgatctatgat
gcctccagtttgaaaagtggggtcccatcaaggttcagcggcagtggatc
tgggacagatttcactctcaccatcagcagcctgcagcctgaagattttg
caacttattactgtcaacagtttaatagttactggacgttcggccaaggg
accaaggtggaaatcaaa

2D5 V<sub>L</sub> Amino Acid Sequence (SEQ ID NO:10)
AIQLTQSPSSLSASVGDRVTITCRASQGISSALAWYQQKPGKAPKLLIYD
ASSLKSGVPSRFSGSGSGTDFTLTISSLQPEDFATYYCQQFNSYWTFGQG
TKVEIK

2H4 V<sub>H</sub> Nucleic Acid Sequence (SEQ ID NO:11)
gaggtgcacctggtggagtctgggggaggcttggtccagcctggggggtc
cctgagactctcctgtgcagcctctggattccacctttagtagctattgga
tgagctgggtccgccaggctccagggaaagggctggagtgggtggccaac
ataaatcaatatggaagtgagaaatactatgtggactctgtgaagggccg
attcaccatctccagagacaacgccaagaactcgctgtatctgcaaatga
acagcctgagagccgaggacacggctgtgtattactgtgcgagggactcc
ccgtattactatggttcggggagttattatagaggatactggtacttcga
tctctggggccgtggcaccctggtcactgtctcctca

2H4 V<sub>H</sub> Amino Acid Squence (SEQ ID NO:12)
EVHLVESGGGLVQPGGSLRLSCAASGFTFSSYWMSWVRQAPGKGLEWVAN
INQYGSEKYYVDSVKGRFTISRDNAKNSLYLQMNSLRAEDTAVYYCARDS
PYYYGSGSYYRGYWYFDLWGRGTLVTVSS

2H4 V<sub>L</sub> Nucleic Acid Squence (SEQ ID NO:13)
gacatccagatgacccagtctccatcctcactgtctgcatctgtaggaga
cagagtcaccatcacttgtcgggcgagtcagggtattagcagctggttag
cctggtatcagcagaaaccagagaaagcccctaagtccctgatctatgct
gcatccagtttgcaaagtggggtcccatcaaggttcagcggcagtggatc
tgggacagatttcactctcaccatcagcagcctgcagcctgaagattttg
caacttattactgccaacagtataatagttaccctcccaccttcggccaa
gggacacgactggagattaaa

2H4 V<sub>L</sub> Amino Acid Squence (SEQ ID NO:14)
DIQMTQSPSSLSASVGDRVTITCRASQGISSWLAWYQQKPEKAPKSLIYA
ASSLQSGVPSRFSGSGSGTDFTLTISSLQPEDFATYYCQQYNSYPPTFGQ
GTRLEIK

5D5 V<sub>H</sub> nucleic acid Squence (SEQ ID NO:15)
caggtgcagctggtggagtctgggggaggcgtggtccagcctggggaggtc
cctgagactctcctgtgcagcgtctggattcaccttcagtagctatggca
tgcactgggtccgccaggctccaggcaaggggctggagtgggtggcagtt
atatggtatgatggaagtaataaatactatgcagactccgtgaagggccg
attcaccatctccagagacaattccaagaacacgctgtatctgcaaatga
acagcctgagagccgaggacacggctgtgtattactgtgcgagagaggt
aatcgtagccactatatacccttgcctactggggccagggaaccctggt
caccgtctcctca

5D5 V<sub>H</sub> Amino Acid Squence (SEQ ID NO:16)
QVQLVESGGGVVQPGRSLRLSCAASGFTFSSYGMHWVRQAPGKGLEWVAV
IWYDGSNKYYADSVKGRFTISRDNSKNTLYLQMNSLRAEDTAVYYCAREG
NRSHYIPFAYWGQGTLVTVSS

5D5 V<sub>L</sub> Nucleic Acid Squence (SEQ ID NO:17)
gacatccagatgacccagtctccatcctcactgtctgcatctgtaggaga
cagagtcaccatcacttgtcgggcgagtcagggtattagcagctggttag
cctggtatcagcagaaaccagagaaagcccctaagtccctgatctatgct
gcatccagtttgcaaagtggggtcccatcaaggttcagcggcagtggatc
tgggacagatttcactctcaccatcagcagcctgcagcctgaagattttg
caacttattactgccaacagtataatagttacccgcgcacttcggcgga
gggaccaaggtggagatcaaa 5D5 V$_L$ Amino Acid Squence (SEQ ID NO:18)
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYPRTFGG

GTKVEIK

Example 5A

ELISA Assay to Determine HuMAb 5E8 Binding Characteristics on Anthrax Protective Antigen A standard ELISA was performed as described, in section *Characterization of Binding of Human Monoclonal Antibodies to Protective Antigen*, supra. Plates were coated with either PA 83 or PA 63, and bound antibody was detected using alkaline phosphatase-conjugated goat anti-human IgG (Fc specific) (Jackson Immunoresearch Laboratories, West Grove, Pa.). ELISA binding curves were generated for HuMAb 5E8 to full length PA 83 and to the active fragment of PA (i.e., PA 63).

Figure 14:
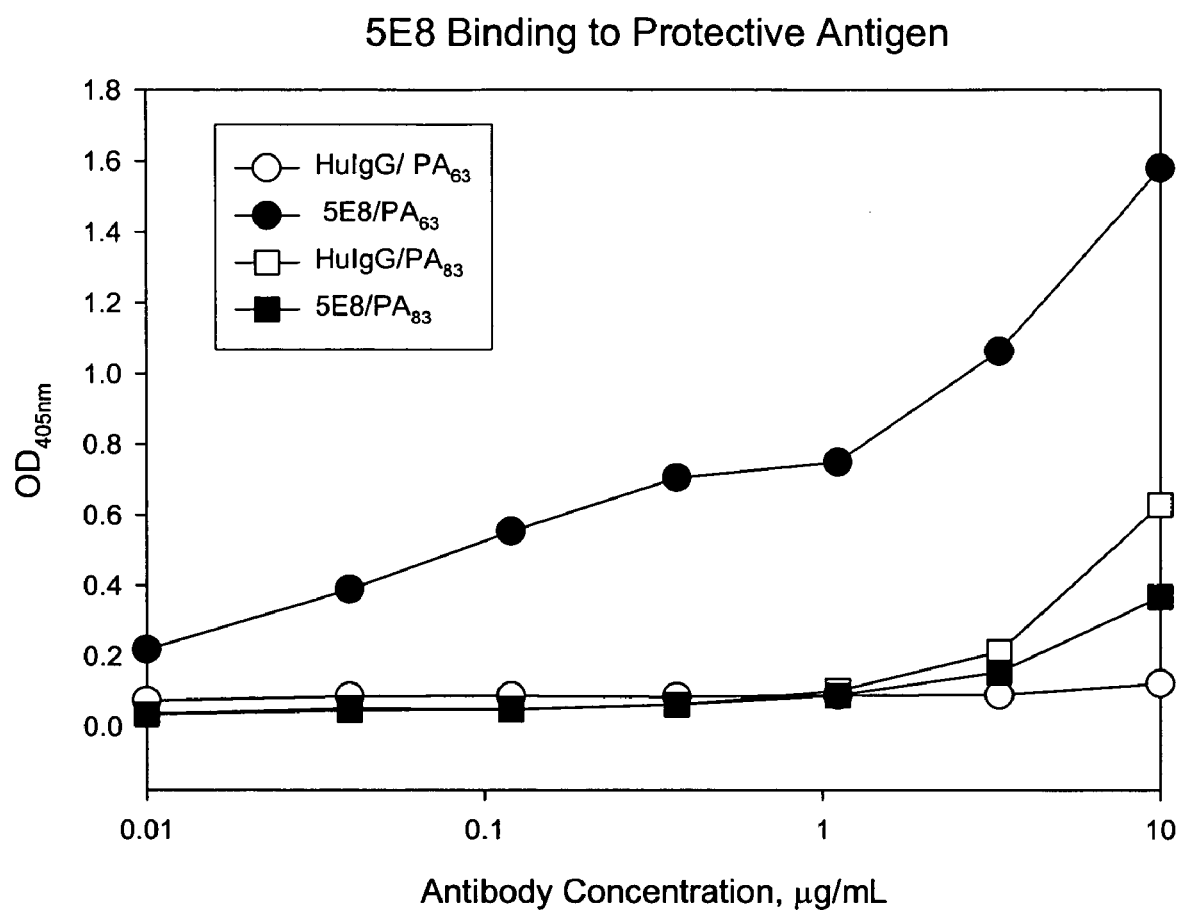
FIG. 14 is a graph showing comparison of binding of HuMAb 5E8 to PA 63 and PA 83 using a standard ELISA assay.

The results show that HuMab 5E8 binds PA 63, but demonstrated no appreciable binding to PA 83 in the ELISA assay (see FIG. 14). Therefore, HuMAb 5E8 would not have been selected for further development if ELISA binding to PA83 was used as a primary screen, which methodology has been used previously for screening antibodies against protective antigen (see Little et al., 1988, Infection and Immunity, 56:1807-1813).

Example 5B

ELISA Assay to Determine HuMAb 5E8 Binding Characteristics on Anthrax Protective Antigen A standard ELISA was performed as described, in section *Characterization of Binding of Human Monoclonal Antibodies to Protective Antigen*, supra. Human antibody 5E8 was incubated together with each of murine antibody 14B7, 2D5 and 1G3 (Little et al., 1996, Microbiology 142:707-715) on a plate coated with PA 63. Binding of the mouse antibody to the PA is detected with a goat anti-mouse IgG (Fc specific) alkaline phosphatase conjugate (Jackson ImmunoResearch Laboratories, West Grove, Pa.).

The results demonstrate that none of the murine MAbs were blocked from binding to PA63 as a result of the binding of HuMAb 5E8 to PA 63 (see FIG. 15). This indicates that none of these murine antibodies competes directly with 5E8 for binding to PA 63, thus suggesting that the 5E8 antibody binds to a different epitope on PA 63.

Example 6

Pharmacokinetics of Human IgG After Intravenous and Subcutaneous Administration to Rabbits This Example evaluates the pharmacokinetics of human IgG after intravenous and subcutaneous administration of human monoclonal antibodies in rabbits. The data were generated to support the selection of a dosing regimen for studies to evaluate the efficacy of a human monoclonal antibody against anthrax protective antigen in a lethal inhalation anthrax model in the rabbit.

Human IgG was administered either intravenously (2 rabbits) or subcutaneously (4 rabbits) to determine the pharmacokinetics of human monoclonal antibodies in rabbits. An intravenous dose of 10 mg/kg was administered to 2 rabbits and a subcutaneous dose of 10 mg/kg was administered to 4 rabbits. The Cmax (maximum concentrations) was 389 µg/mL and 155 µg/mL after intravenous and subcutaneous administration, respectively. The Tmax (time to maximum concentration) after intravenous injection was 2 hours. The Tmax after subcutaneous administration was 48 hours. Serum concentrations greater than 100 µg/mL were observed 4 days after both intravenous and subcutaneous administration and levels greater than 20 µg/mL wereas observed after 14 days. Adequate serum levels were achieved after both subcutaneous and intravenous administrations, and either dosing route is appropriate in efficacy studies. To maintain such adequate serum levels over prolonged periods, a loading dose of antibody can be administered initially, followed by a lower second dose of the antibody can be administered approximately 4 days after the initial dose. However, the increased time to maximal concentration should be taken into consideration when performing subcutaneous injections in a therapeutic model.

Example 7A

Efficacy and Therapeutic Treatment of Human Monoclonal Antibodies Against a Lethal Aerosol Challenge of *Bacillus anthracis* (Ames Strain) in a Rabbit Inhalation Model This Example demonstrates the efficacy of anti-PA antibodies of the invention in a lethal inhalation anthrax model in the rabbit. Twenty-six out of 30 rabbits treated with antibody 5D5 or 5E8 survived after 14 days post-exposure to anthrax. Thus, antibodies of the invention provide an effective new treatment for exposure to anthrax.

Ten New Zealand White Rabbits in four groups were administered one of two monoclonal anti-PA antibodies (PA mAb 5E8 or 5D5) immediately following and 96 hours post aerosol challenge with *Bacillus anthracis*. Aerosolized spores were delivered via muzzle only inhalation at a dose of approximately 100 times LD$_{50}$. Animals were observed for mortality during a 14 day post exposure period. Protection by the antibody against anthrax infection is defined as an increased time-to-death or as a two week survival post challenge. Table 3 below provides an evaluation of the efficacy of the human monoclonal antibodies, including number of rabbits in the study groups, dosage level of antibody administered 1 hour after exposure, dosage level of antibody 96 hours after exposure, and the number of rabbits surviving the study.

TABLE 3

| No. of Rabbits | Control or Antibody | Dose Level 1 hour post exposure | Dose Level 96 hours post exposure | Survival |
| --- | --- | --- | --- | --- |
| 10 | Saline | 0 mg/kg | 0 mg/kg | None |
| 10 | 5D5 | 6 mg/kg | 3 mg/kg | 9/10 |
| 10 | 5E8 | 6 mg/kg | 3 mg/kg | 9/10 |
| 10 | 5E8 | 12 mg/kg | 5 mg/kg | 8/10 |

Figure 16:
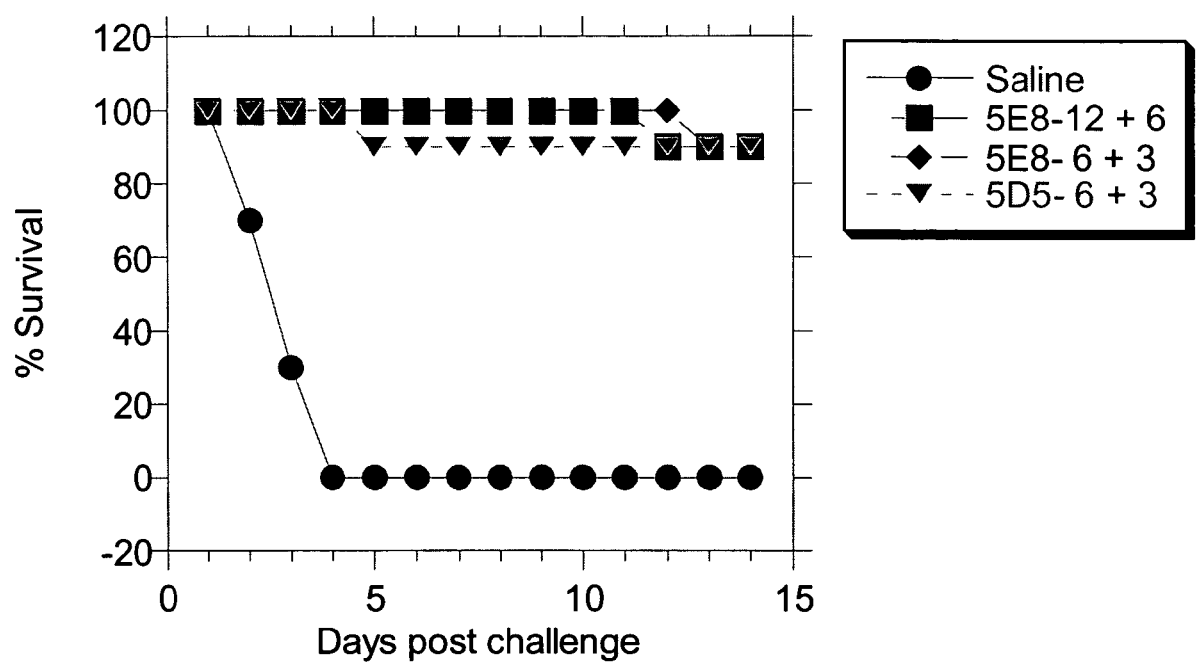
FIG. 16 is a graph showing efficacy of HuMAbs 5E8 and 5D5 in a rabbit inhalation model.

The study results, shown in FIG. 16, demonstrate the efficacy of the fully human antibodies of the invention in the rabbit. Animals in the control group died within 5 days of exposure to *Bacillus anthracis*. An extended survival time (14 days) was seen in 85% of animals treated with mAb 5E8. A single rabbit receiving 6 mg/kg 5E8 died on day 14, one rabbit receiving 12 mg/kg of 5E8 died on day 13 and one rabbit receiving 12 mg/kg died on day 14. A single rabbit treated with 3 mg/kg 5D5 died within 5 days of exposure. Pharmacokinetic analysis of serum samples from the rabbits indicates that the plasma levels of the antibodies were greater than 70 μg/mL during the first 24 hours after administration. Plasma levels in the groups treated with 6 mg/kg declined to between 50 and 117 μg/mL prior to the booster dose of 3 mg/kg and were less than 30 μg/mL by the end of the study. This demonstrates that plasma levels of the anti-PA antibodies above 50 μg/mL are sufficient to protect rabbits in this model. As the lowest dose administered in this study was efficacious, it is likely that lower plasma concentrations may also be effective.

Example 7B

Efficacy of the Human Monoclonal Antibody (5E8) Against a Lethal Aerosol Challenge of *Bacillus anthracis* (Ames Strain) in a Rabbit Inhalation Model This Example demonstrates the efficacy of lower dose levels of anti-PA antibodies of the invention in a lethal inhalation anthrax model in the rabbit. Seventeen out of 20 rabbits treated with antibody 5E8 survived after 14 days post-exposure to anthrax. Thus, antibodies of the invention provide an effective treatment for exposure to anthrax.

Ten New Zealand White Rabbits in two groups were administered monoclonal anti-PA antibody (PA mAb 5E8) immediately following and 96 hours post aerosol challenge with *Bacillus anthracis*. Aerosolized spores were delivered via muzzle only inhalation at a dose of approximately 100 times $LD_{50}$. Animals were observed for mortality during a 14 day post exposure period. Protection by the antibody against anthrax infection is defined as an increased time-to-death or as a two week survival post challenge. Table 4 below provides an evaluation of the efficacy of the human monoclonal antibodies, including number of rabbits in the study groups, dosage level of antibody administered 1 hour after exposure, dosage level of antibody 96 hours after exposure, and the number of rabbits surviving the study.

TABLE 4

| No. of Rabbits | Control or Antibody | Dose Level 1 hour post exposure | Dose Level 96 hours post exposure | Survival |
|---|---|---|---|---|
| 10 | Saline | 0 mg/kg | 0 mg/kg | None |
| 10 | 5E8 | 1 mg/kg | 1 mg/kg | 9/10 |
| 10 | 5E8 | 3 mg/kg | 3 mg/kg | 8/10 |

Figure 17:
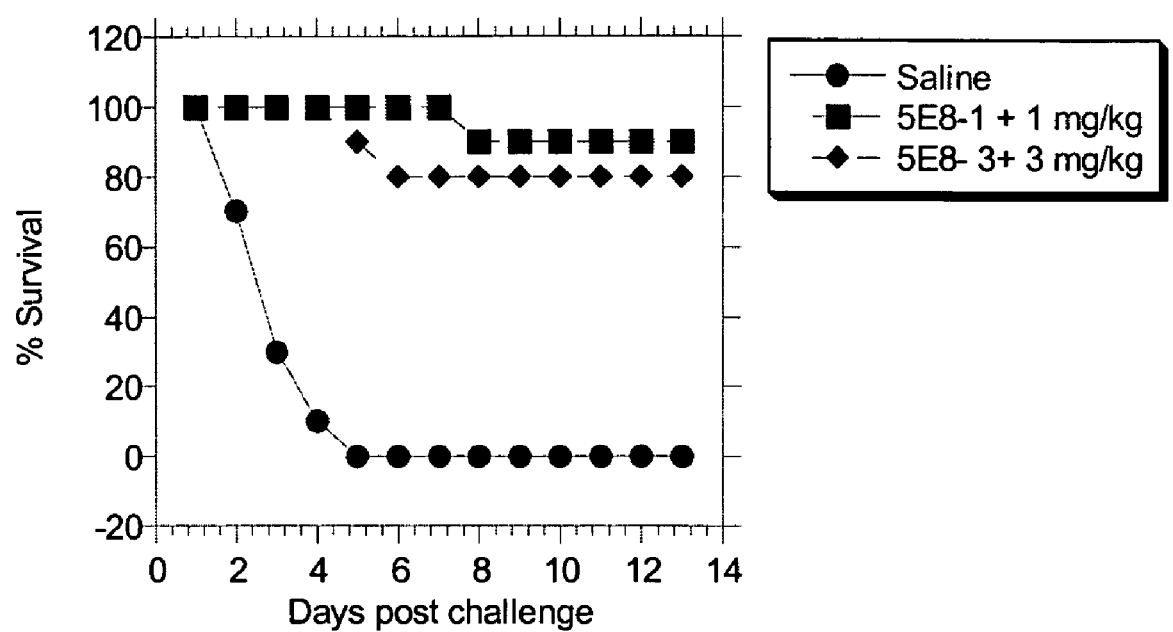
FIG. 17 is a graph showing efficacy of HuMAb 5E8 at lower doses in a rabbit inhalation model.

The study results, shown in FIG. 17, demonstrate the efficacy of the fully human antibodies of the invention in the rabbit. Animals in the control group died within 5 days of exposure to *Bacillus anthracis*. An extended survival time (14 days) was seen in 85% of animals treated with mAb 5E8. A single rabbit receiving 1 mg/kg 5E8 died within 8 days of exposure. One rabbit treated with 3 mg/kg died on day 5 and one died on day 6. The increased survival rates in this study indicated that dose levels as low as 1 mg/kg are efficacious in preventing mortality in this animal model.

Example 7C

Therapeutic Treatment of the Human Monoclonal Antibody (5E8) Against a Lethal Aerosol Challenge of *Bacillus anthracis* (Ames Strain) in a Rabbit Inhalation Model This Example demonstrates the efficacy of anti-PA antibodies of the invention in preventing mortality after clinical signs of exposure have initiated in a lethal inhalation anthrax model in the rabbit. Nine of 10 rabbits treated with antibody 5E8 twenty-four hours after exposure to anthrax survived for 14 days. Three of 5 rabbits treated with antibody 5E8 forty-eight hours after exposure to anthrax survived for 14 days. These animals had measurable signs of infection prior to treatment. Thus, antibodies of the invention provide an effective treatment for exposure to anthrax.

Ten New Zealand White Rabbits were administered monoclonal anti-PA antibody (PA mAb 5E8) 24 hours post aerosol challenge with *Bacillus anthracis* and 10 rabbits were administered monoclonal anti-PA antibody (PA mAb 5E8) 48 hours post aerosol challenge. Aerosolized spores were delivered via muzzle only inhalation at a dose of approximately 100 times $LD_{50}$. Animals were observed for mortality during a 14 day post exposure period. Protection by the antibody against anthrax infection is defined as an increased time-to-death or as a two week survival post challenge. Table 5 below provides an evaluation of the efficacy of the human monoclonal antibodies, including number of rabbits in the study groups, dosage level of antibody, time of administration in relation to anthrax challenge, and the number of rabbits surviving the study.

TABLE 5

| Number of Rabbits | Antibody | Schedule of Treatments | Dose Level (mg/kg) | | Survival |
|---|---|---|---|---|---|
| | | | $1^{st}$ | $2^{nd}$ | |
| 10 | Saline | 1, 72 hours post exposure | 0 | 0 | 0/10 |
| 10 | 5E8 | 24, 120 hours post exposure | 10 | 10 | 8/9[a] |
| 10 | 5E8 | 48, 144 hours post exposure | 10 | 10 | 3/5[b] |

[a]One animal was removed from the study for humane reasons unrelated to exposure to anthrax or the monoclonal antibody.
[b]Five animals died from anthrax within 48 hours of exposure and, therefore, did not receive treatment with the monoclonal antibody.

Figure 18:
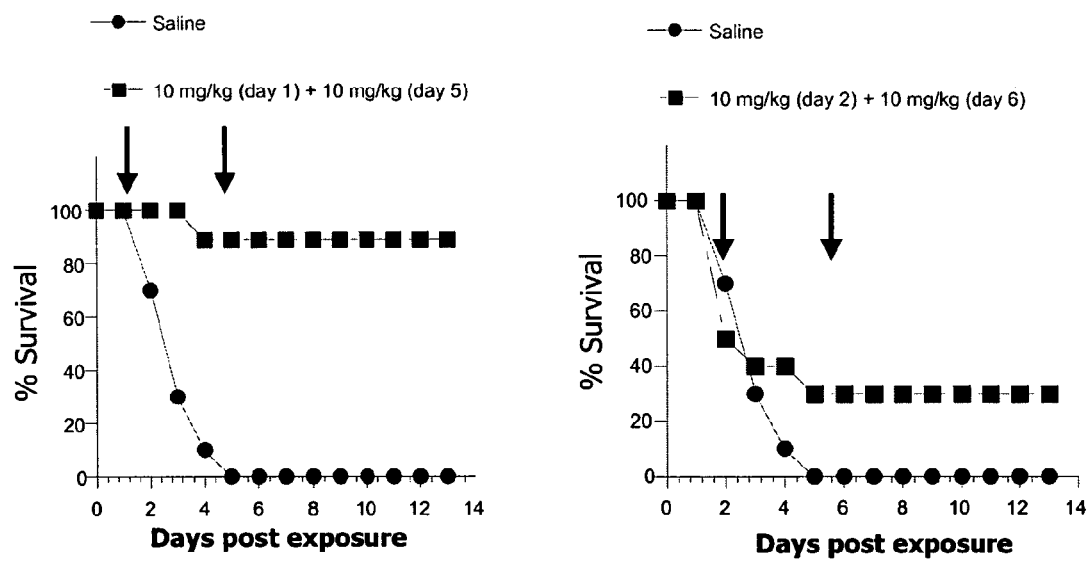
FIG. 18 are graphs showing efficacy of HuMAb 5E8 administered post-exposure in a rabbit inhalation model. (A) Animals treated 24 hrs and 5 days post exposure. (B) Animals treated 48 hrs and 6 days post exposure.

The study results demonstrate the efficacy of the fully human antibodies of the invention after the development of signs of anthrax in the rabbit (see FIG. 18). A decrease in circulating levels of neutrophils (absolute number and relative percentage of neutrophils) was observed in the majority of the control animals at 24 hours post-exposure to anthrax. These parameters were also evaluated at this timepoint in the animals treated with 5E8 at 24 hours post-exposure to anthrax and were decreased in all of the animals. Among the five animals treated with the monoclonal antibody at 48 hours post-exposure to anthrax, four of the animals had decreased appetite and the other animal had decreased activity prior to treatment.

In this study, animals in the control group died within 5 days of exposure to *Bacillus anthracis* while 8 of the 9 animals treated at 24 hours survived and 3 of the 5 symptomatic animals treated at 48 hours survived. Combined, this data provides evidence that the monoclonal antibody is effective at treating animals after the clinical course of the disease has initiated.

Equivalents

Those skilled in the art will recognize, or be able to ascertain using no more than routine experimentation, many equivalents of the specific embodiments of the invention described herein. Such equivalents are intended to be encompassed by the following claims.

Incorporation by Reference

All patents, pending patent applications and other publications cited herein are hereby incorporated by reference in their entirety.

We claim:

1. An isolated monoclonal antibody comprising a heavy chain variable region comprising the amino acid sequence set forth in SEQ ID NO:2, wherein the antibody specifically binds to human B. anthracis protective antigen.

2. An isolated monoclonal antibody comprising a light chain variable region comprising the amino acid sequence set forth in SEQ ID NO:4, wherein the antibody specifically binds to B. anthracis protective antigen.

3. An isolated monoclonal antibody or antigen binding portion thereof comprising:
   (a) heavy chain variable regions CDR1, CDR2, and CDR3 comprising the amino acid sequences of SEQ ID NO: 24, 22, and 20, respectively; and
   (b) light chain variable regions CDR1, CDR2, and CDR3 comprising the amino acid sequences of SEQ ID NO: 30, 28, and 26, respectively;
   wherein the antibody binds to B. anthracis protective antigen.

4. An isolated monoclonal antibody or antigen binding portion thereof, comprising a heavy chain variable region and a light chain variable region, wherein the sequences of the heavy chain variable region and the light chain variable region, respectively, comprise the sequences of SEQ ID NOs: 2 and 4, and wherein the antibody specifically binds to B. anthracis protective antigen.

5. The monoclonal antibody of claims 1, 2, 3, or 4, wherein the antibody is human.

6. An isolated monoclonal antibody which specifically binds with an affinity of at least $10^7$ M$^{-1}$ to an epitope on B. anthracis protective antigen recognized by the antibody of claim 3 or 4.

7. The antibody of claim 3, which neutralizes a Bacillus anthracis toxin in a toxin neutralization assay.

8. The antibody of claim 7, where the toxin neutralization assay employs a cell from a tissue selected from nervous, heart, lung, and bone marrow.

9. The antibody of claim 8, where the cell is a macrophage.

10. The antibody of claim 3, comprising a human IgG heavy chain and a human kappa light chain.

11. The antibody of claim 3, comprising an IgG1 or IgG3 heavy chain.

12. The antibody of claim 3, wherein the antibody is a Fab fragment or a single chain antibody (scFv).

13. The antibody of claim 7 wherein the ability of the antibody to neutralize the toxin requires binding to Fc receptor.

14. The antibody of claim 3, wherein the antibody exhibits higher affinity for PA63 over PA 83 according to standard ELISA.

15. The antibody of claim 3, wherein the antibody:
   (1) does not bind PA 83 at 1 µg/ml, OD$_{405\ nm}$ 0.2 or less according to standard ELISA;
   (2) does not block anthrax lethal factor or edema factor binding to PA.

16. The antibody of claim 3, wherein the antibody does not compete with an anti-PA antibody selected from murine 1G3, murine 2D5 and murine 14B7 in binding to PA 63.

17. A method of inhibiting a physiological activity of B. anthracis protective antigen, comprising contacting B. anthracis protective antigen with an effective amount of the antibody of claim 3, such that the physiological activity of the protective antigen is inhibited.

18. A method of neutralizing a B. anthracis toxin, comprising contacting B. anthracis protective antigen with an effective amount of the antibody of claim 3, such that the toxin is neutralized.

19. A method of treating anthrax in a host infected with B. anthracis, comprising administering to the host the antibody of claim 3 in an amount effective to treat anthrax.

20. The method of claim 19, further comprising administering an additional therapeutic agent.

21. The method of claim 20, wherein the additional therapeutic agent is selected from an antibiotic and vaccine.

22. A method for detecting the presence of B. anthracis protective antigen in a sample comprising:
   contacting the sample with the antibody of claim 3, under conditions which allow for formation of a complex comprising the antibody and the protective antigen; and
   detecting the formation of the complex.

23. A pharmaceutical composition comprising the antibody of claim 3, and a pharmaceutically acceptable carrier.

24. A method for treating or preventing anthrax in a patient in need of such treatment, comprising the step of administering the antibody of claim 3 in a dosage from 0.1 mg/kg to 100 mg/kg.

25. A method for treating or preventing anthrax in a patient in need of such treatment, comprising the step of administering the antibody of claim 3 in a dosage from 0.3 mg/kg to 50 mg/kg.

26. A method for treating or preventing anthrax in a patient in need of such treatment, comprising the step of administering the antibody of claim 3 in a dosage from 1 mg/kg to 12 mg/kg.

27. The method according to claim 24, wherein the patient is infected with *B. anthracis*.

28. The method according to claim 27, wherein the patient exhibits neutropenia.

29. The method according to claim 27, wherein the patient exhibits one or more signs and/or symptoms of anthrax infection.

30. The method according to claim 24, wherein the patient is not infected with *B. anthracis*.

31. The method according to claim 24, wherein the dosage is administered subcutaneously or intravenously.

32. The method according to claim 24, wherein one or more additional dosages is administered.

* * * * *

UNITED STATES PATENT AND TRADEMARK OFFICE
CERTIFICATE OF CORRECTION

PATENT NO. : 7,456,264 B2  Page 1 of 1
APPLICATION NO. : 10/850635
DATED : November 25, 2008
INVENTOR(S) : Tibor Keler et al.

It is certified that error appears in the above-identified patent and that said Letters Patent is hereby corrected as shown below:

At column 6, line 63, please change "$V_H$-region" to --$V_L$-region--

At column 6, line 65, please change "SEQ ID NO: 9" to --SEQ ID NO: 7--

At column 6, line 66, please change "SEQ ID NO: 10" to --SEQ ID NO: 8--

At column 7, line 1, please change "SEQ ID NO: 11" to --SEQ ID NO: 9--

At column 7, line 2, please change "SEQ ID NO: 12" to --SEQ ID NO: 10--

At column 7, line 4, please change "SEQ ID NO: 13" to --SEQ ID NO: 11--

At column 7, line 5, please change "SEQ ID NO: 14" to --SEQ ID NO: 12--

At column 7, line 7, please change "SEQ ID NO: 15" to --SEQ ID NO: 13--

At column 7, line 8, please change "SEQ ID NO: 16" to --SEQ ID NO: 14--

At column 7, line 10, please change "SEQ ID NO: 17" to --SEQ ID NO: 15--

At column 7, line 11, please change "SEQ ID NO: 18" to --SEQ ID NO: 16--

At column 7, line 14, please change "SEQ ID NO: 19" to --SEQ ID NO: 17--

At column 7, line 15, please change "SEQ ID NO: 20" to --SEQ ID NO: 18--

Signed and Sealed this
First Day of February, 2011

David J. Kappos
*Director of the United States Patent and Trademark Office*